United States Patent
Rajagopalan et al.

(10) Patent No.: US 10,580,173 B2
(45) Date of Patent: Mar. 3, 2020

(54) GRAPHICAL DISPLAY OF PHYSIOLOGICAL PARAMETERS ON PATIENT MONITORS

(71) Applicant: SHENZHEN MINDRAY BIO-MEDICAL ELECTRONICS CO., LTD., Nanshan, Shenzhen (CN)

(72) Inventors: Cadathur Rajagopalan, Dumont, NJ (US); Scott Eaton, Briarcliff Manor, NY (US)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 0 days.

(21) Appl. No.: 16/018,519

(22) Filed: Jun. 26, 2018

(65) Prior Publication Data

US 2018/0300913 A1    Oct. 18, 2018

Related U.S. Application Data

(63) Continuation-in-part of application No. 15/878,245, filed on Jan. 23, 2018, now Pat. No. 10,096,137, which is a continuation of application No. 14/543,651, filed on Nov. 17, 2014, now Pat. No. 9,875,560.

(Continued)

(51) Int. Cl.
*G06T 11/20* (2006.01)
*G16H 15/00* (2018.01)
(Continued)

(52) U.S. Cl.
CPC ............ *G06T 11/203* (2013.01); *A61B 5/742* (2013.01); *G06F 19/00* (2013.01); *G06T 11/206* (2013.01);
(Continued)

(58) Field of Classification Search
None
See application file for complete search history.

(56) References Cited

U.S. PATENT DOCUMENTS 9,778,079 B1 * 10/2017 Al-Ali ..................... G01D 7/02
9,875,560 B2    1/2018 Rajagopalan
(Continued)

OTHER PUBLICATIONS

'A Survey of Radial Methods for Information Visualization', by Geoffrey M. Draper, Yarden Livnat, and Richard F. Riesenfeld, IEEE Transactions on Visualization and Computer Graphics, vol. 15, No. 5, pp. 759-776, Sep./Oct. 2009. (Year: 2009).*

*Primary Examiner* — James A Thompson
(74) *Attorney, Agent, or Firm* — Kory D. Christensen

(57) ABSTRACT

A system includes a parameter acquisition unit that receives one or more physiological parameters from one or more sensors. A memory device stores historical values of the one or more physiological parameters received by the parameter acquisition unit. A user interface unit displays representations of current and historical values of the one or more physiological parameters in a graphical user interface (GUI), wherein the GUI includes a semicircular gauge having a curved portion representing a common range of values for the one or more physiological parameters and a radial axis representing time, a center of the semicircular gauge corresponding to an earliest time for which a historical value is represented within the semicircular gauge and the curved portion corresponding to a current time. The GUI further includes a numerical representation of a current value of each physiological parameter displayed at a corresponding point along the curved portion of the semicircular gauge and a trend line for each physiological parameter originating at the center of the semicircular gauge and extending toward the curved portion thereof, wherein each trend line graphs historical values for a respective physiological parameter, and wherein a point on the trend line representing a historical value has a radial coordinate related to time and an angular coordinate related to the historical value.

38 Claims, 28 Drawing Sheets

Related U.S. Application Data

(60) Provisional application No. 61/905,029, filed on Nov. 15, 2013, provisional application No. 61/970,740, filed on Mar. 26, 2014.

(51) Int. Cl.

| | | |
|---|---|---|
| *G16H 40/63* | (2018.01) | |
| *G16H 50/30* | (2018.01) | |
| *G16H 40/60* | (2018.01) | |
| *A61B 5/00* | (2006.01) | |
| *G06F 19/00* | (2018.01) | |
| *A61B 5/024* | (2006.01) | |
| *A61B 5/021* | (2006.01) | |

(52) U.S. Cl.
CPC ............ G16H 15/00 (2018.01); G16H 40/63 (2018.01); G16H 50/30 (2018.01); *A61B 5/021* (2013.01); *A61B 5/024* (2013.01); *A61B 5/746* (2013.01); *G06T 2210/41* (2013.01); *G16H 40/60* (2018.01)

(56) References Cited

U.S. PATENT DOCUMENTS

| | | | |
|---|---|---|---|
| 2006/0287586 A1 | 12/2006 | Murphy | |
| 2009/0054743 A1 | 2/2009 | Stewart | |
| 2009/0222286 A1 | 9/2009 | Elsholz | |
| 2009/0262131 A1* | 10/2009 | Suntinger | G06Q 10/06 345/619 |
| 2011/0201911 A1 | 8/2011 | Johnson | |
| 2011/0282705 A1 | 11/2011 | Vucina | |
| 2013/0045685 A1 | 2/2013 | Kiani | |
| 2014/0081659 A1* | 3/2014 | Nawana | G16Z 99/00 705/3 |
| 2014/0135588 A1 | 5/2014 | Al-Ali | |
| 2015/0025329 A1 | 1/2015 | Amarasingham | |
| 2016/0055319 A1* | 2/2016 | Ikegaya | G06F 19/328 705/3 |
| 2017/0000426 A1 | 1/2017 | Harper | |
| 2017/0042488 A1* | 2/2017 | Muhsin | A61B 5/742 |

\* cited by examiner

GRAPHICAL DISPLAY OF PHYSIOLOGICAL PARAMETERS ON PATIENT MONITORS

RELATED APPLICATIONS

This application is a continuation-in-part of U.S. patent application Ser. No. 15/878,245, filed Jan. 23, 2018, for "Graphical Display of Physiological Parameters on Patient Monitors," which is a continuation of U.S. patent application Ser. No. 14/543,651, filed Nov. 17, 2014, for "Graphical Display of Physiological Parameters on Patient Monitors," which claims the benefit of priority to U.S. Provisional Patent Application No. 61/905,029, titled "Graphical Display of Physiological Parameters on Patient Monitors," filed on Nov. 15, 2013 and U.S. Provisional Patent Application No. 61/970,740, titled "Graphical Display of Physiological Parameters on Patient Monitors," filed on Mar. 26, 2014, all of which are incorporated by reference in their entireties.

TECHNICAL FIELD

This disclosure relates to systems and techniques that help a clinician or other user quickly comprehend current, recent, and/or historical physiological parameters via a graphical representation.

SUMMARY

A system for displaying physiological parameters of a patient includes a parameter acquisition unit that receives one or more physiological parameters from one or more sensors. The system further includes a memory device that stores historical values of the one or more physiological parameters received by the parameter acquisition unit. The system also includes a user interface unit displays representations of current and historical values of the one or more physiological parameters in a graphical user interface (GUI), wherein the GUI includes a semicircular gauge having a curved portion representing a common range of values for the one or more physiological parameters and a radial axis representing time, a center of the semicircular gauge corresponding to an earliest time for which a historical value is represented within the semicircular gauge and the curved portion corresponding to a current time. The GUI further includes a numerical representation of a current value of each physiological parameter displayed at a corresponding point along the curved portion of the semicircular gauge and a trend line for each physiological parameter originating at the center of the semicircular gauge and extending toward the curved portion thereof, wherein each trend line graphs historical values for a respective physiological parameter, and wherein a point on the trend line representing a historical value has a radial coordinate related to time and an angular coordinate related to the historical value.

DETAILED DESCRIPTION

Figure 1:
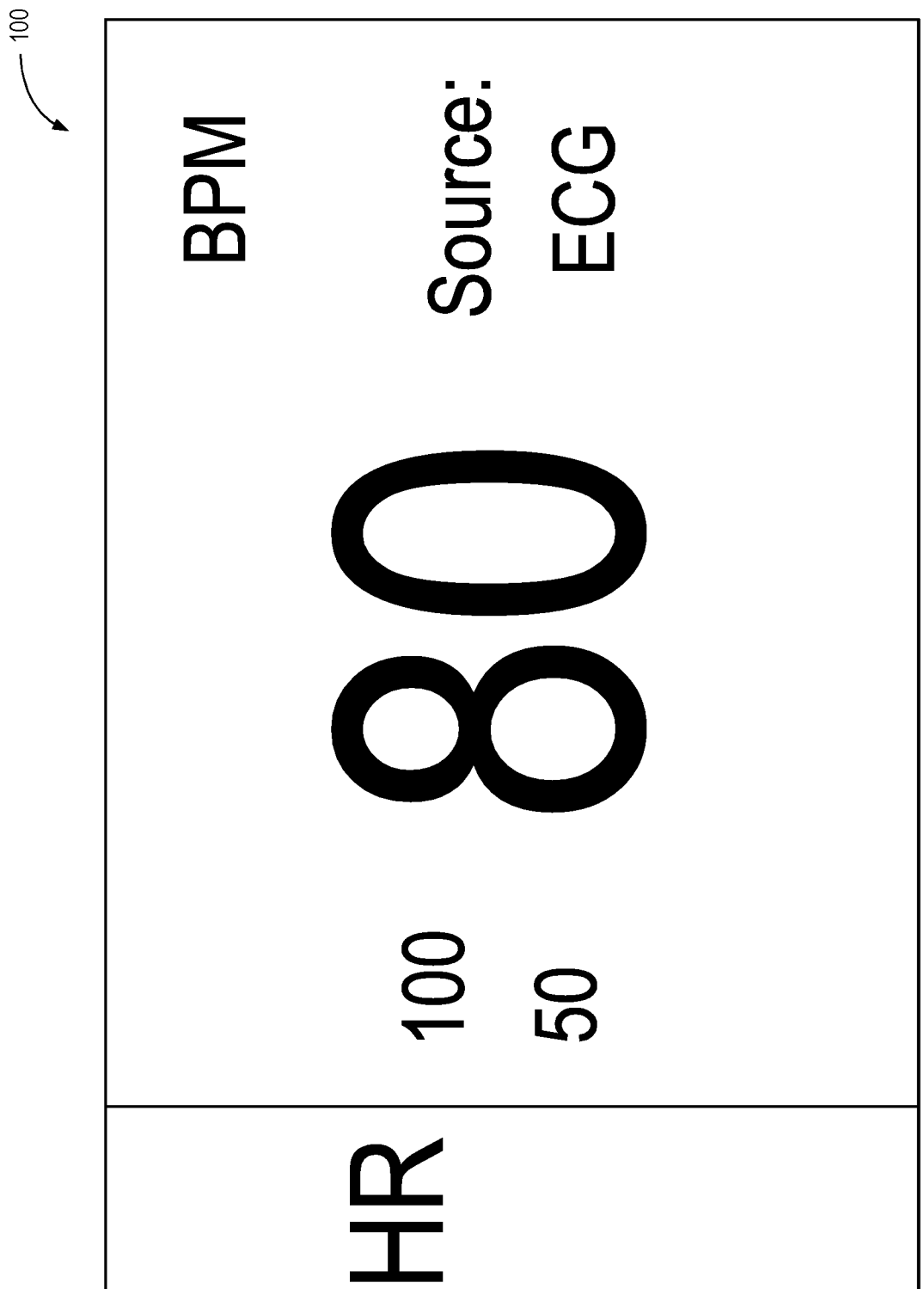
FIG. 1 is a tiled display of a measured heart rate parameter that may be displayed on a physiological parameter monitoring equipment, according to one embodiment.

This disclosure generally relates to techniques to help a clinician or other user quickly comprehend current, recent, and/or historical physiological parameters via a graphical representation. In various embodiments, one or more physiological parameters are determined or received by a system configured to process and present related information to a user, such as a clinician or other healthcare worker or interested party. The physiological parameters may be received by the system via a network or other data connection. In other embodiments, the system may include one or more connections ports for probes and/or sensors for measuring patient physiological parameters.

The physiological parameters are displayed via an electronic display. The physiological parameters may be shown with a visual comparison with historical physiological parameters, custom alarms, predefined thresholds, and/or the like.

For example, the electronic display may allow for a quick comparison of a current physiological parameter with threshold (high and/or low) values, historical values, values from a previous time period, normal values, normalized values, general averages, patient-specific averages, multiple stages of alarm levels, target values, danger zones, custom alarms, and the like.

In some embodiments, historical data may be presented as a ghost image. The ghost image may be a single historical value or an average of historical values during a time period. The time period may be user selectable or may be predefined as a number of minutes, hours, days, weeks, or even years. Multiple historical values may be displayed using multiple ghost images of historical values (averages, relative, or absolute) from prior time periods.

Historical data may also be illustrated as a line, a graph, and/or other feature as described herein. Alarms limits, thresholds, and maximum and minimum values may be shown as numerical values and/or by representation through the use of one or more icons or symbols. Similarly, the current value of a physiological parameter may be shown as a numeric value and/or through representation by a graphic, an icon, and/or a symbol.

In various embodiments, the electronic display may be configured to display a semicircle, a semi-ellipse, a partial circle, a partial ellipse, a rectangle, a square, a triangle, or any other geometric shape or n-side polygon. In various embodiments, the display may be a custom shape that has any number of curves and/or sides.

A physiological parameter presentation system may be computerized and may include, incorporate, utilize, and/or otherwise rely on various processors, memory, software modules, hardware components, electronic connectors, ports, communication components, and the like. An electronic input receiver may receive electronic values corresponding to measured physiological parameters. In some embodiments, the system may receive the values of physiological parameters via a data or network connection. In other embodiments, the system may include probe and/or sensor ports for connection to probes and/or sensors for measuring physiological parameters.

The physiological parameter presentation system may include a data store to store historical values. The data store may be remote and accessible via a network connection and/or locally accessible. The system may generate a graphical display via a display module. The display module may be implemented as a software program, hardware circuitry, and/or a combination thereof.

The display module may generate a graphical display of the physiological parameter(s) that includes one or more of a range of possible values for the physiological parameter, a visual representation of one or more threshold values, a numerical display of the current value of the measured physiological parameter, and a historical comparator based on one or more of the historical values of the measured physiological parameter. The generated graphical display may then be output to an electronic display for visualization by a clinician or other user.

In various embodiments, the historical comparator is a ghost image of a historical value of the physiological parameter. In some embodiments, the historical comparator is a ghost image of an average of historical values of the physiological parameter during a prior time period. The time period may be user-selected, adjusted, and/or a predefined preset.

In some embodiments, the historical comparator is an extent indicator (e.g., an arrow, a line, a bar, etc.) that indicates a minimum historical value and a maximum historical value of the physiological parameter during a prior time period. In other embodiments, the historical comparator is a trend line showing past values. For example, the trend line may be a line that extends from a current value of the physiological parameter on an outer perimeter of a semicircle to a base of the semicircle, such that the most recent historical values are positioned closest to the outer perimeter of the semicircle and the oldest historical values are positioned closest to the base of the semicircle.

As previously described, the graphical display may show minimum and maximum possible values of the physiological parameters in rectangular, circular, semicircular, and/or other gauge shapes. An extend indicator, a ghost image, and/or a trend line may be shown on rectangular, circular, semicircular, and/or other gauge shapes.

The embodiments of the disclosure are described below with reference to the drawings, wherein like parts are designated by like numerals throughout. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor do the steps or sequences of steps need to be executed only once or even in the same order in subsequent repetitions.

Embodiments may include various steps, which may be embodied in machine-executable instructions to be executed by a computer system. A computer system includes one or more general-purpose or special-purpose computers (or other electronic devices). The computer system may include hardware components that include specific logic for performing the steps or may include a combination of hardware, software, and/or firmware.

Embodiments may also be provided as a computer program product including a computer-readable medium having stored thereon instructions that may be used to program a computer system or other electronic device to perform the processes described herein. The computer-readable medium may include, but is not limited to: hard drives, floppy diskettes, optical disks, CD-ROMs, DVD-ROMs, ROMs, RAMs, EPROMs, EEPROMs, magnetic or optical cards, solid-state memory devices, or other types of media/computer-readable media suitable for storing electronic instructions.

Computer systems and the computers in a computer system may be connected via a network. Suitable networks for configuration and/or use as described herein include one or more local area networks, wide area networks, metropolitan area networks, and/or Internet or IP networks, such as the World Wide Web, a private Internet, a secure Internet, a value-added network, a virtual private network, an extranet, an intranet, or even stand-alone machines which communicate with other machines by physical transport of media. In particular, a suitable network may be formed from parts or entireties of two or more other networks, including networks using disparate hardware and network communication technologies.

One suitable network includes a server and several clients; other suitable networks may contain other combinations of servers, clients, and/or peer-to-peer nodes, and a given computer system may function both as a client and as a server. Each network includes at least two computers or computer systems, such as the server and/or clients. A computer system may include a workstation, laptop computer, disconnectable mobile computer, server, mainframe, cluster, so-called "network computer" or "thin client," tablet, smart phone, personal digital assistant or other hand-held computing device, "smart" consumer electronics device or appliance, medical device, or a combination thereof.

Suitable networks may include communications or networking software, such as the software available from Novell, Microsoft, Artisoft, and other vendors, and may operate using TCP/IP, SPX, IPX, and other protocols over twisted pair, coaxial, or optical fiber cables, telephone lines, radio waves, satellites, microwave relays, modulated AC power lines, physical media transfer, and/or other data transmission "wires" known to those of skill in the art. The network may encompass smaller networks and/or be connectable to other networks through a gateway or similar mechanism.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

As used herein, a software module or component may include any type of computer instruction or computer-executable code located within a memory device. A software module may, for instance, include one or more physical or logical blocks of computer instructions, which may be organized as a routine, program, object, component, data structure, class, etc., that perform one or more tasks or implement particular abstract data types. It is appreciated that a software module may be implemented in hardware and/or firmware instead of or in addition to software. One or more of the functional modules described herein may be separated into sub-modules and/or combined into a single or smaller number of modules.

In certain embodiments, a particular software module may include disparate instructions stored in different locations of a memory device, different memory devices, or different computers, which together implement the described functionality of the module. Indeed, a module may include a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Much of the infrastructure that can be used according to the present invention is already available, such as general purpose computers, computer programming tools and techniques, computer networks and networking technologies, digital storage media, authentication, access control, and other security tools and techniques provided by public keys, encryption, firewalls, and/or other means.

Figure 2:
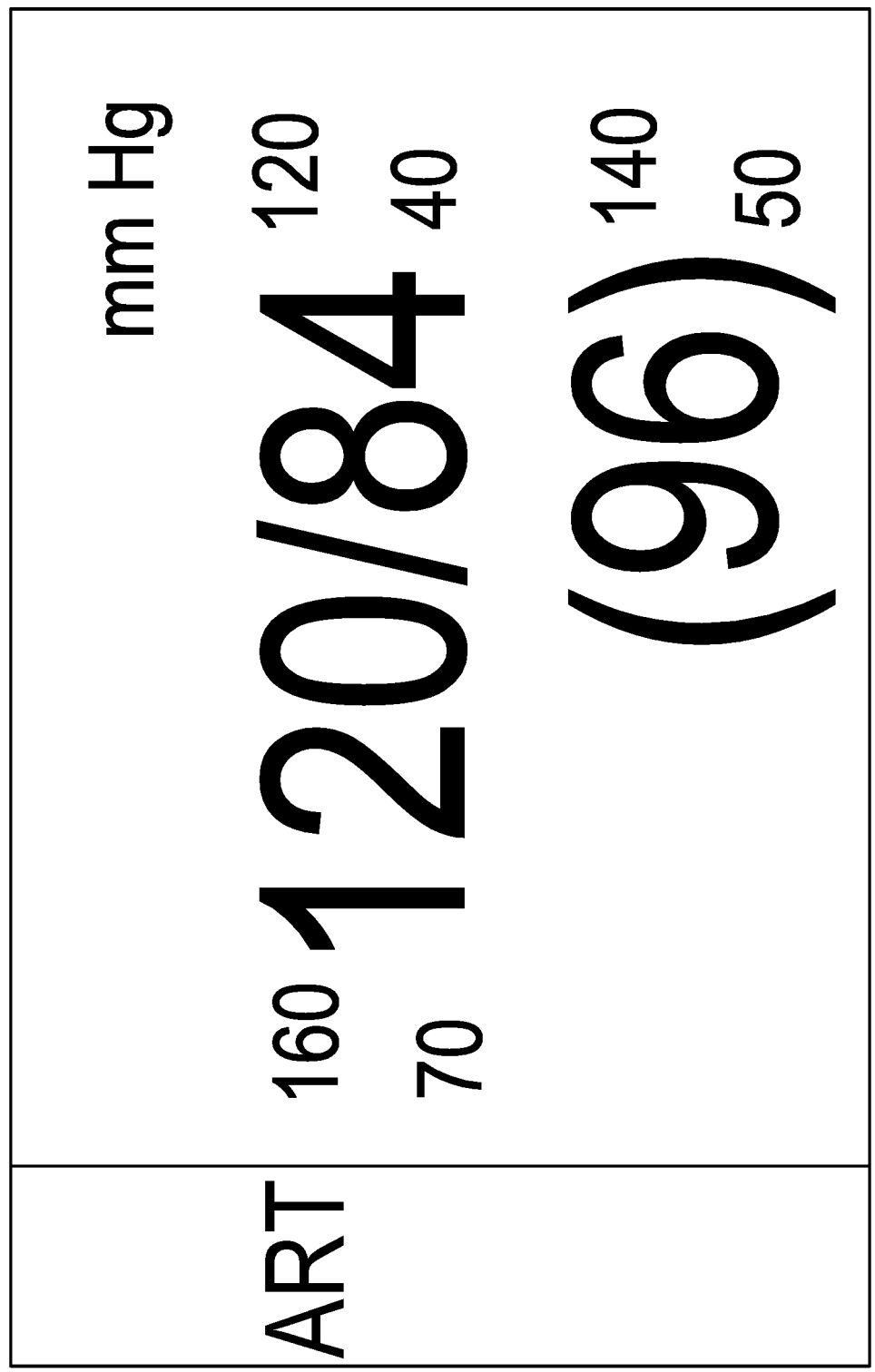
FIG. 2 is a tiled display of a measured blood pressure parameter that may be displayed on a physiological parameter monitoring equipment, according to one embodiment.

FIG. 1 is a tiled display 100 of a measured heart rate parameter that may be displayed on a physiological parameter monitoring equipment, according to one embodiment. The tiled display 100 may show the current value of the physiological parameter, and may include an alarm limit, threshold values, and/or other information. FIG. 2 is a similar tiled display 200 of a measured blood pressure parameter that may be displayed on a physiological parameter monitoring equipment. The physiological parameters of FIGS. 1 and 2 may be displayed on the same display simultaneously or may require toggling between views. To see historical data, alarms, selected threshold values, and other information, the clinician may need to toggle between various screens or display modes.

The present systems and methods allow historical data, alarms, threshold values, and other information to be viewed on the same screen in a format that is quickly understood. The present systems and methods allow for historical variation in a physiological parameter to be viewed concurrently with the current value. Unlike conventional numerical tiles, the present systems and methods allow for multiple high and low alarm limits and/or threshold values to be shown, icons indicating whether or not the physiological parameter is within normal limits, short term trends, range of variation, and the like to be viewed quickly and easily without changing display modes or adjusting display settings.

Example physiological parameters are shown including heart rate, blood pressure, and respiration rates. However, any of a wide variety of physiological parameter information may be used in conjunction with the presently described systems and methods. In fact, other types of data and values may be displayed in a similar manner using the same principles discussed in conjunction with physiological parameter values.

Figure 3:
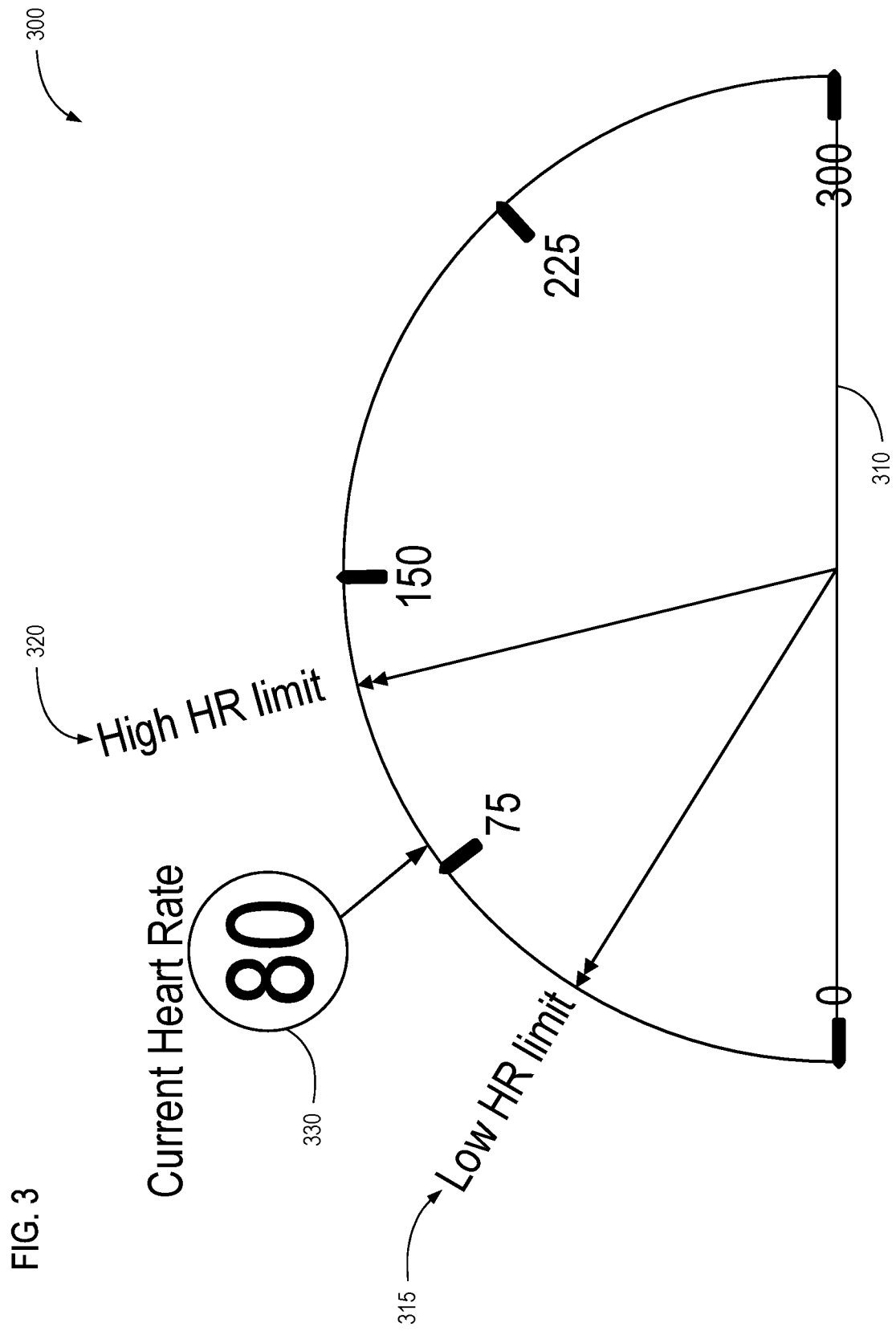
FIG. 3 is one embodiment of a graphical display of a physiological parameter in a semicircle presentation that includes a current value and threshold values.

FIG. 3 is one embodiment of a graphical display 300 of a physiological parameter in a semicircular gauge 310 presentation that includes a current value 330 and threshold values 315 and 320. As illustrated, the semicircular gauge 310 may graphically illustrate the current heart rate 330 relative to the low heart rate limit 315 and the high heart rate limit 320 all simultaneously.

Figure 4:
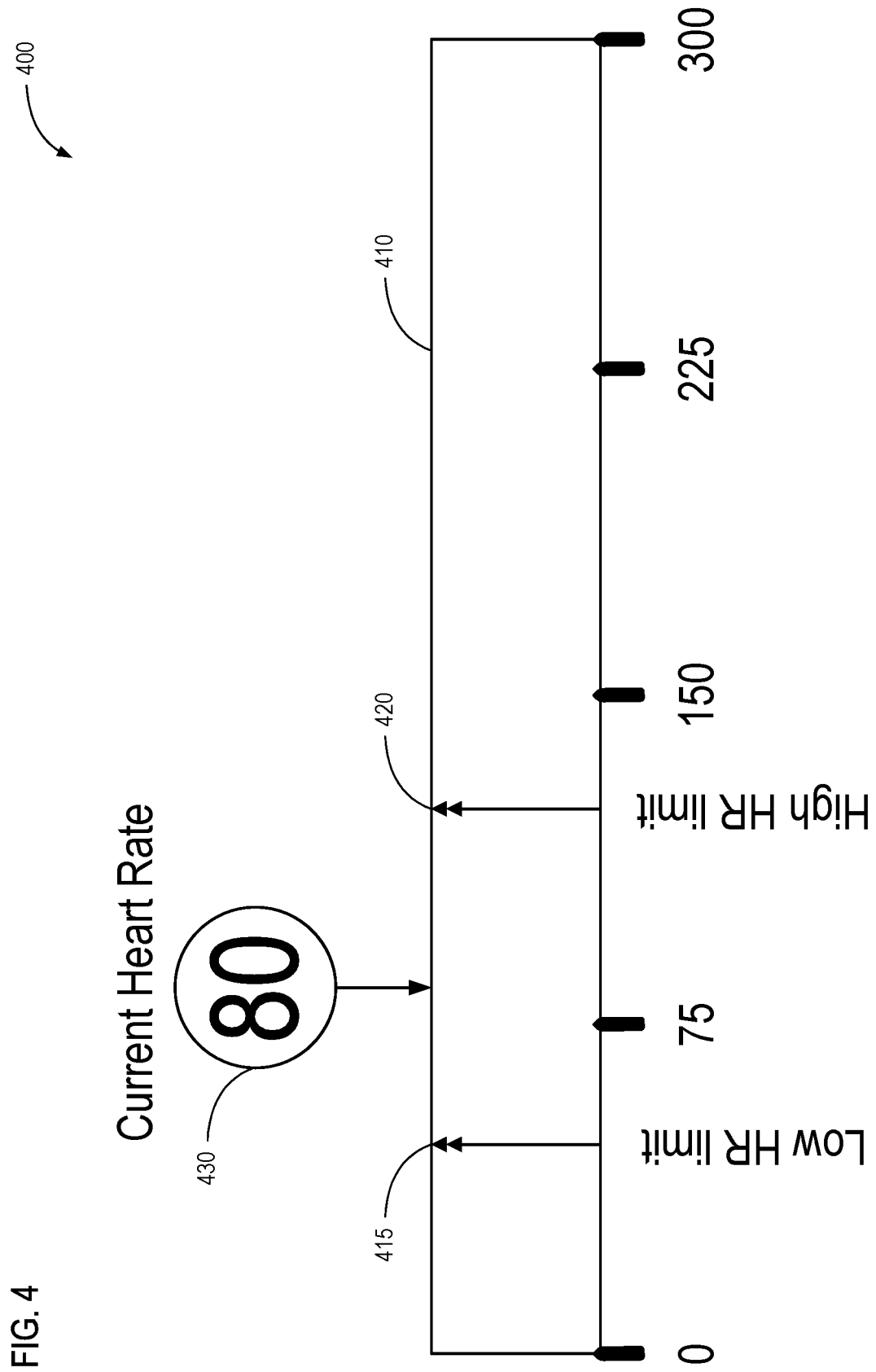
FIG. 4 is another embodiment of a graphical display of a physiological parameter in a rectangular presentation that includes a current value and threshold values.

FIG. 4 is another embodiment of a graphical display 400 of a physiological parameter in a rectangular presentation 410 that includes a current value 430 and threshold values 415 and 420. As illustrated, the current value 430 may be shown as a numerical value. The numerical value may be shown in a geometric shape, or may be colored, shaded, or otherwise highlighted.

Figure 5:
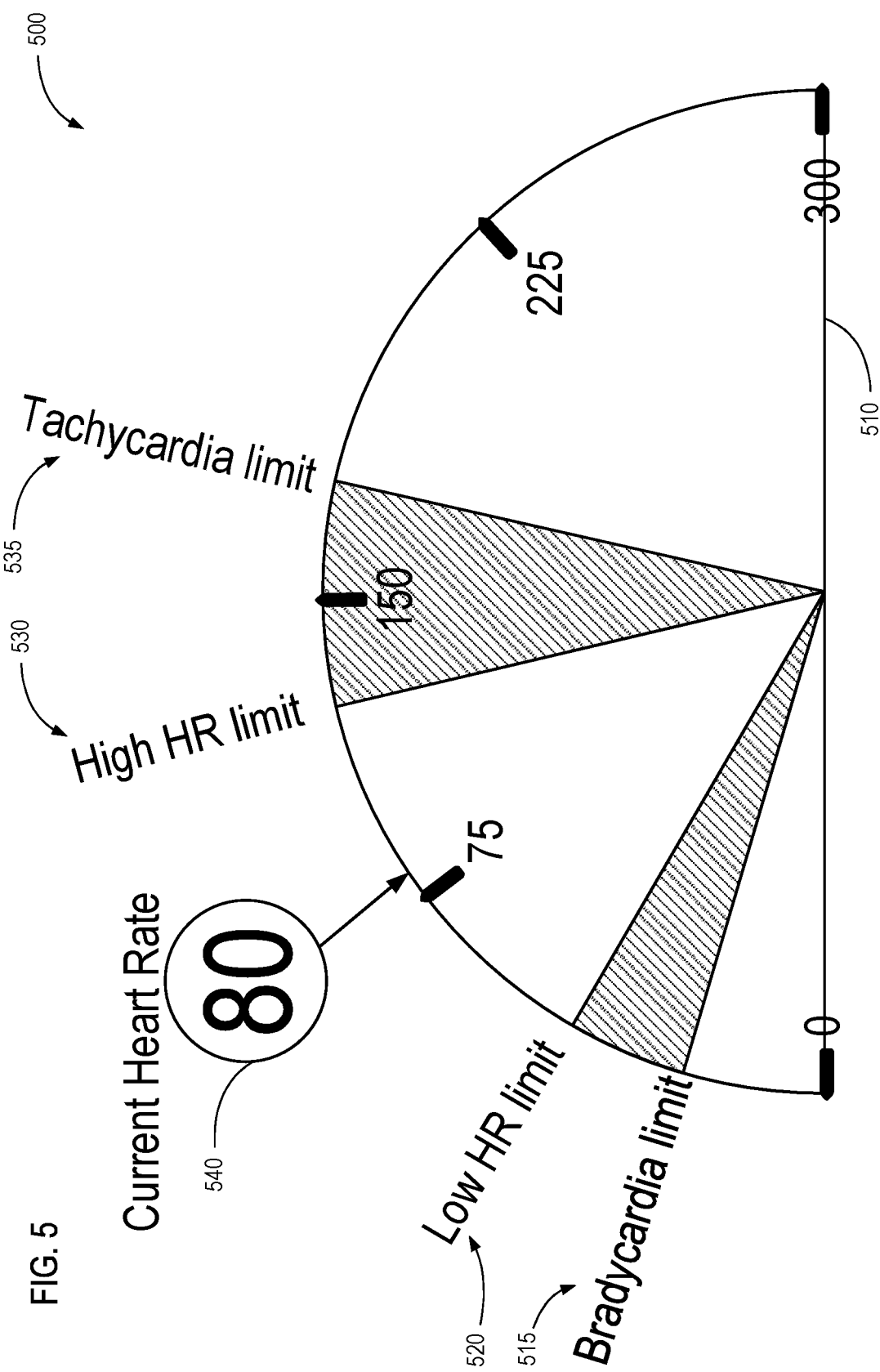
FIG. 5 is an embodiment of a graphical display of a physiological parameter in a semicircle that includes multiple threshold values and physiological parameter threshold zones.

FIG. 5 is an embodiment of a graphical display 500 of a physiological parameter in a semicircle 510 that includes multiple threshold values 515, 520, 530, and 535. The current value 540 of the physiological parameter may be shown along the outside perimeter of the semicircle. The threshold values may define threshold zones for the low values and the high values. Such zones may divide the semicircle into safe zones, warning zones, and danger zones. Alternative and/or additional intermediary zones may be added to the semicircle.

Figure 6:
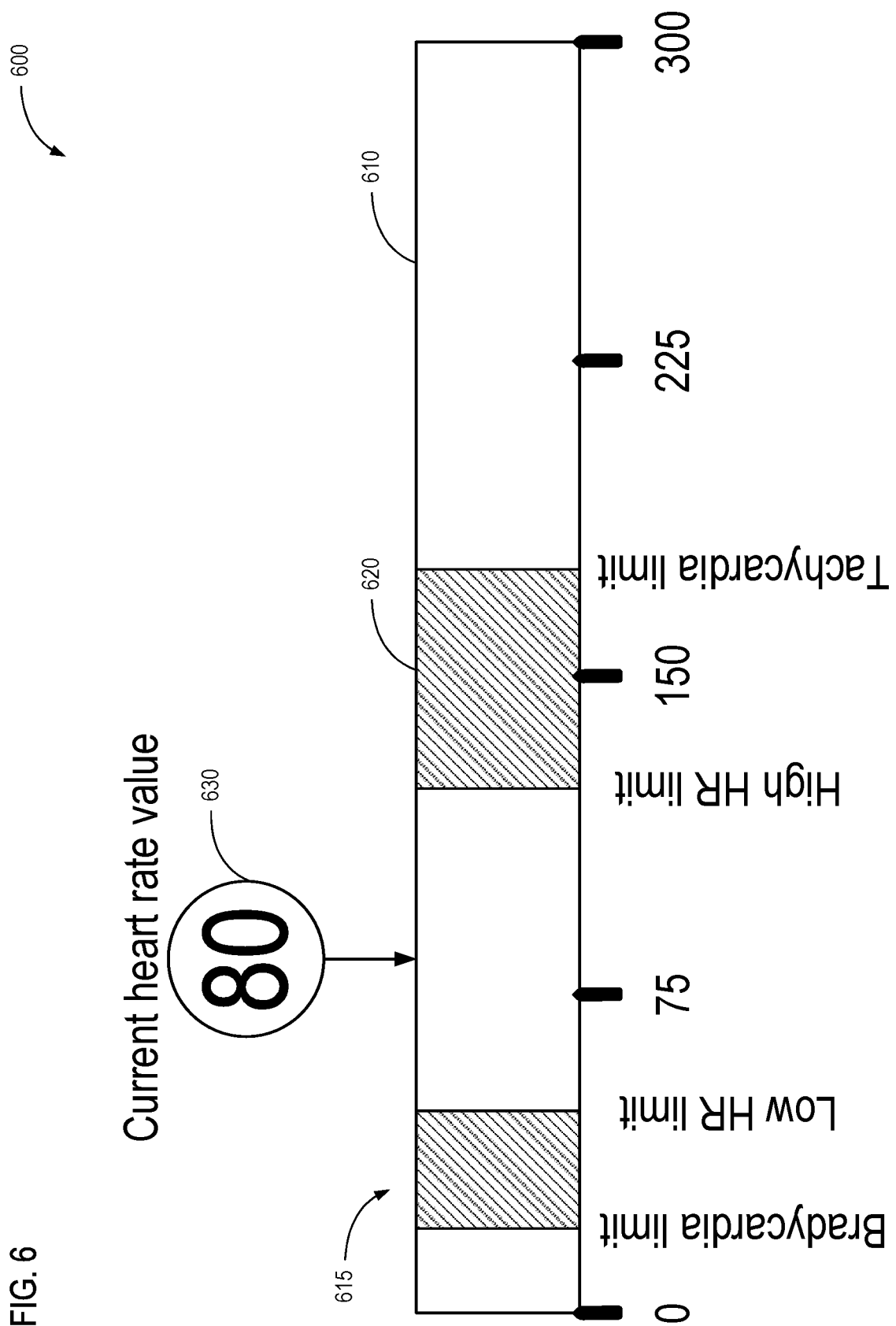
FIG. 6 is an embodiment of a graphical display similar to FIG. 5, in which a rectangle is used instead of a semicircle.

FIG. 6 is an embodiment of a graphical display 600 similar to FIG. 5, in which a rectangular gauge 610 is used instead of a semicircular gauge 510. Similar to FIG. 5, FIG. 6 illustrates a current value 630 of the physiological parameter, lower threshold zones 615 and upper threshold zones 620.

Figure 7:
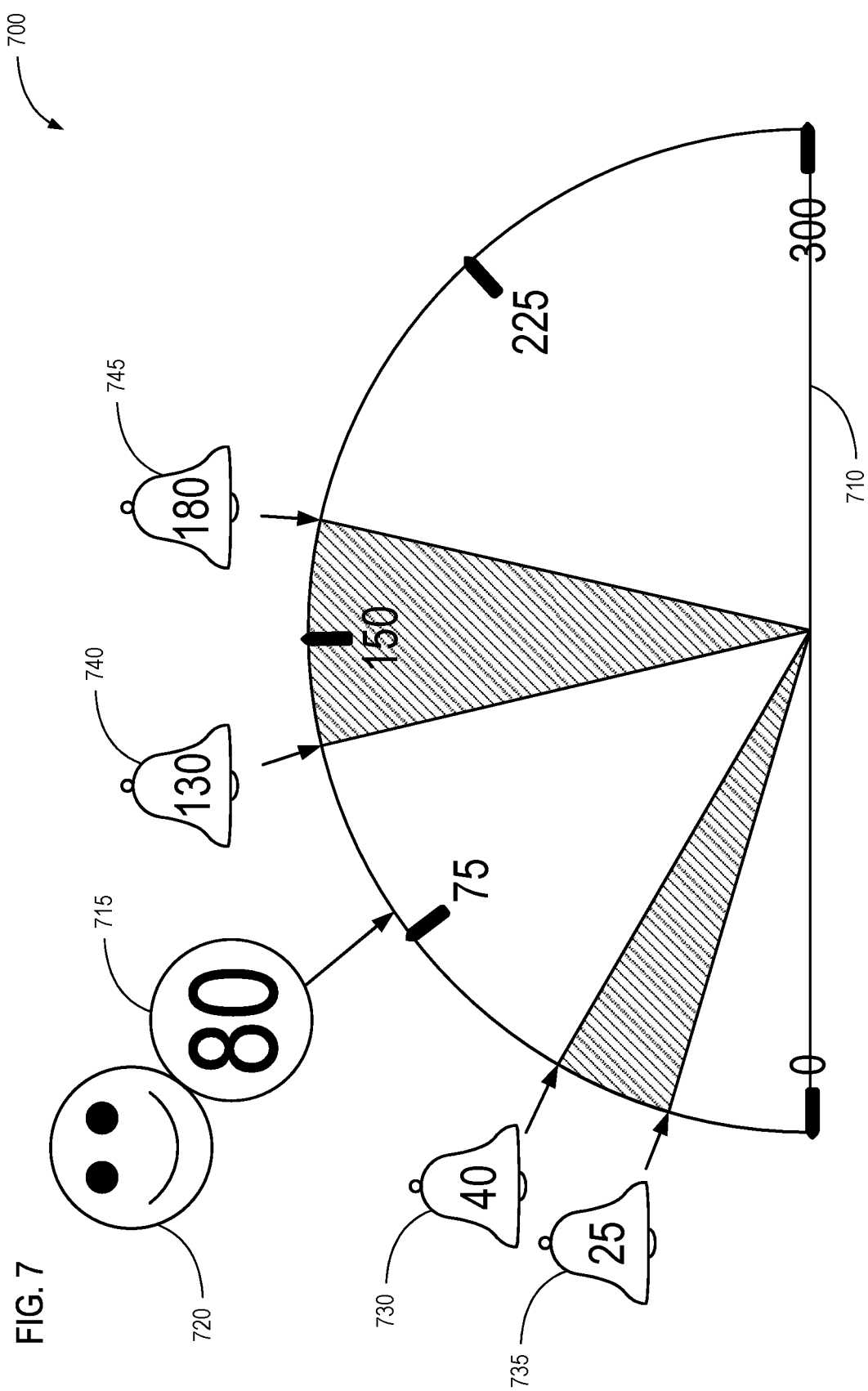
FIG. 7 is an embodiment of a graphical display of physiological parameters in a semicircle t (hat includes multiple limits shown as alarm bells and an icon representing an acceptable status.

FIG. 7 is an embodiment of a graphical display 700 of a physiological parameter in a semicircle 710 that includes multiple limits shown as alarm bells 735, 730, 740, and 745. FIG. 7 also includes a graphical (numerical) display of the current value 715 of the physiological parameter. A status icon 720 (shown as a smiley face) may indicate whether or not the current value 715 of the physiological parameter is in an acceptable range. Different status icons may be used to indicate that the current value 715 is in a warning zone (e.g., a straight face) or danger zone (e.g., a frowny face). In some embodiments, different icons may be used to show that the current value is too low or too high.

Figure 8:
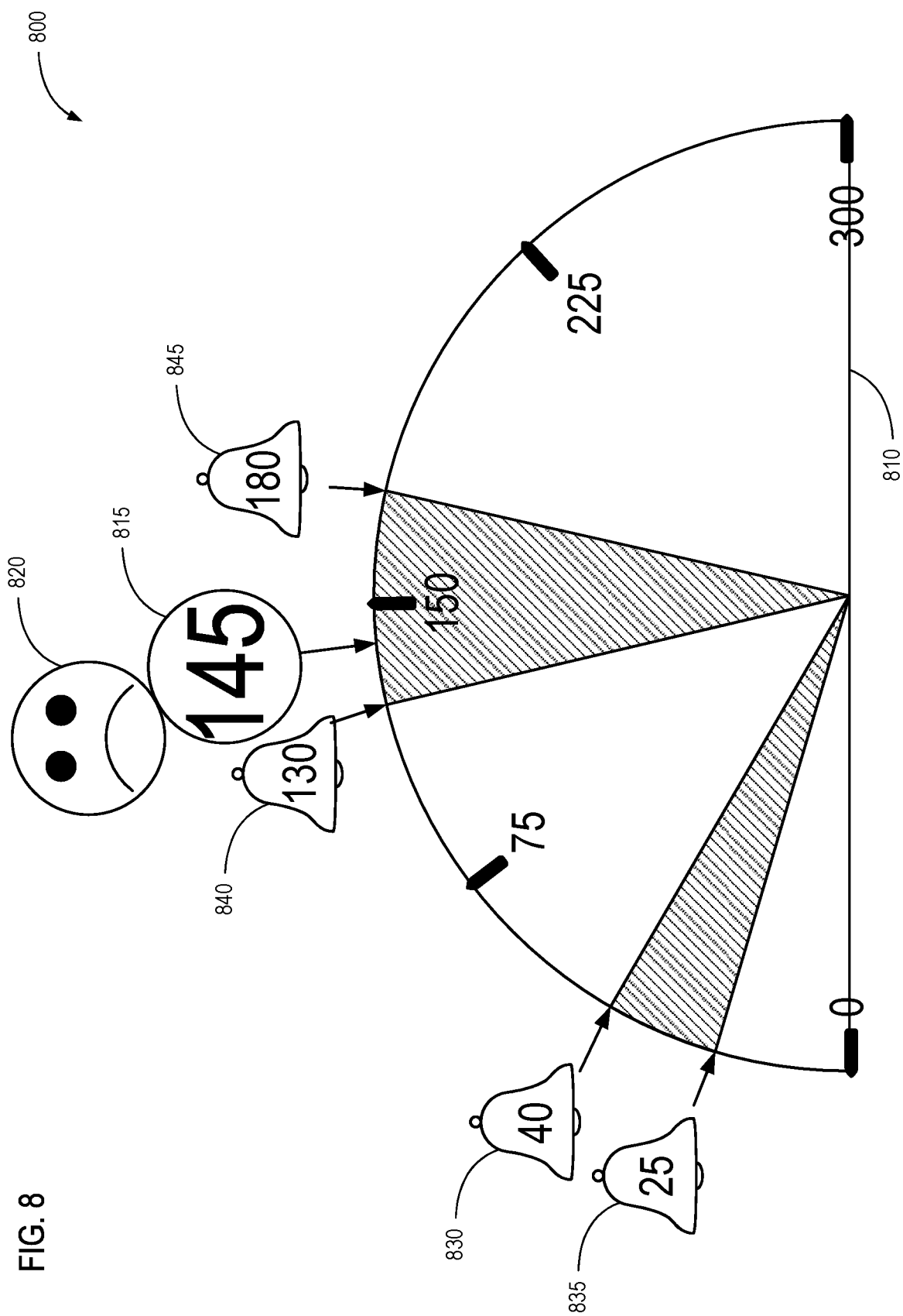
FIG. 8 illustrates the graphical display of FIG. 7 in which the physiological parameter is in an unacceptable zone and is represented by a corresponding icon.

FIG. 8 illustrates a graphical display 800 similar to that of FIG. 7 in which the physiological parameter is in an unacceptable zone (between alarm bells 840 and 845) along the semicircle 810. The status of the current value 815 is represented by a frowny status icon 820. If the current value 815 of the physiological parameter were within the lower zone defined between alarm bells 830 and 835, the same or a different status icon might be used.

Figure 9:
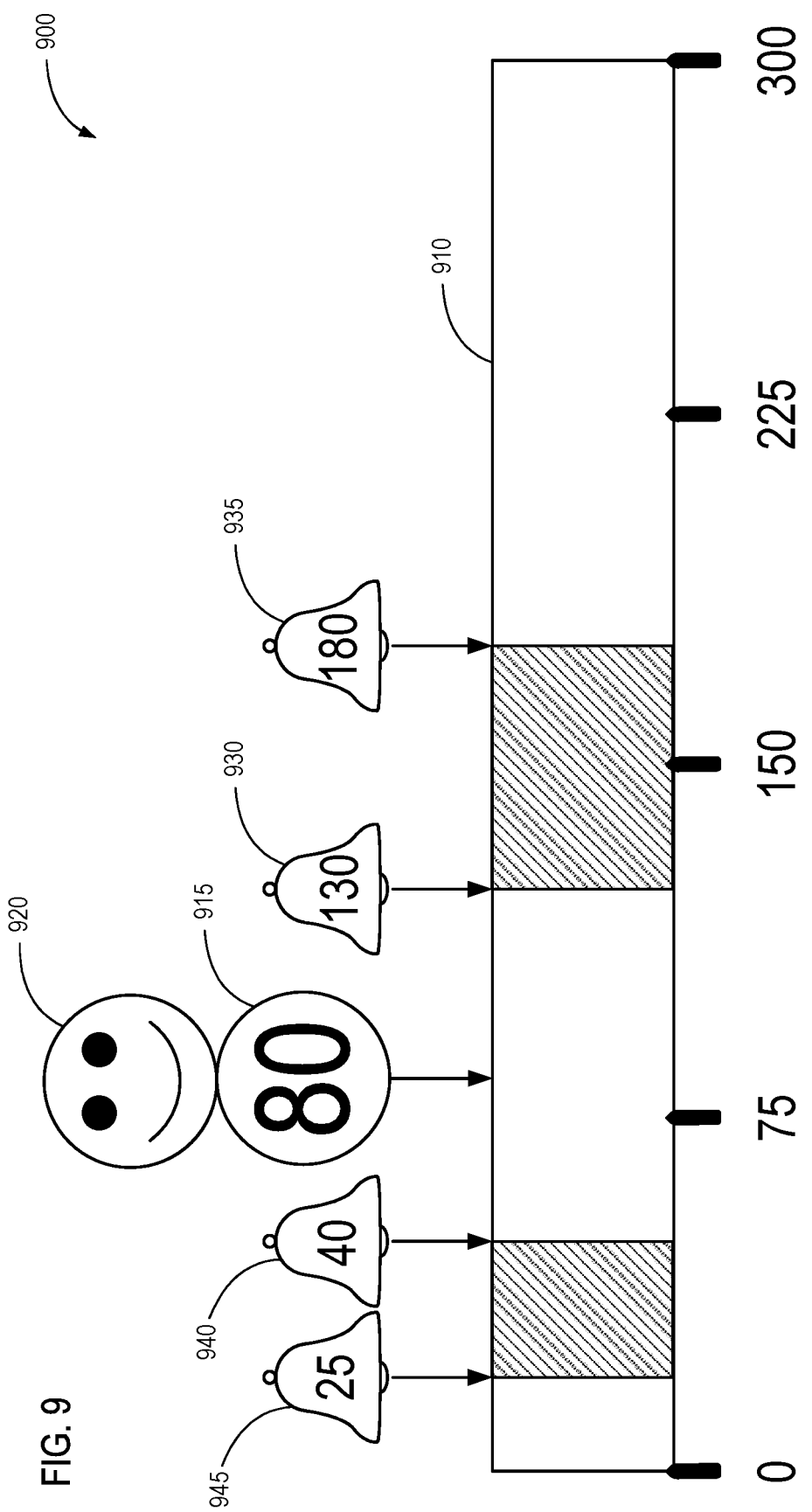
FIG. 9 illustrates a graphical display of a physiological parameter similar to FIG. 7 in a rectangular format.

FIG. 9 illustrates a graphical display 900 of a current value 915 along a rectangular gauge 910 showing the status of a physiological parameter relative to various alarm bells or threshold values 930, 935, 940, and 945. In the illustrated example, the status icon 920 is shown as a smiley face because the current value is within an acceptable zone.

Figure 10:
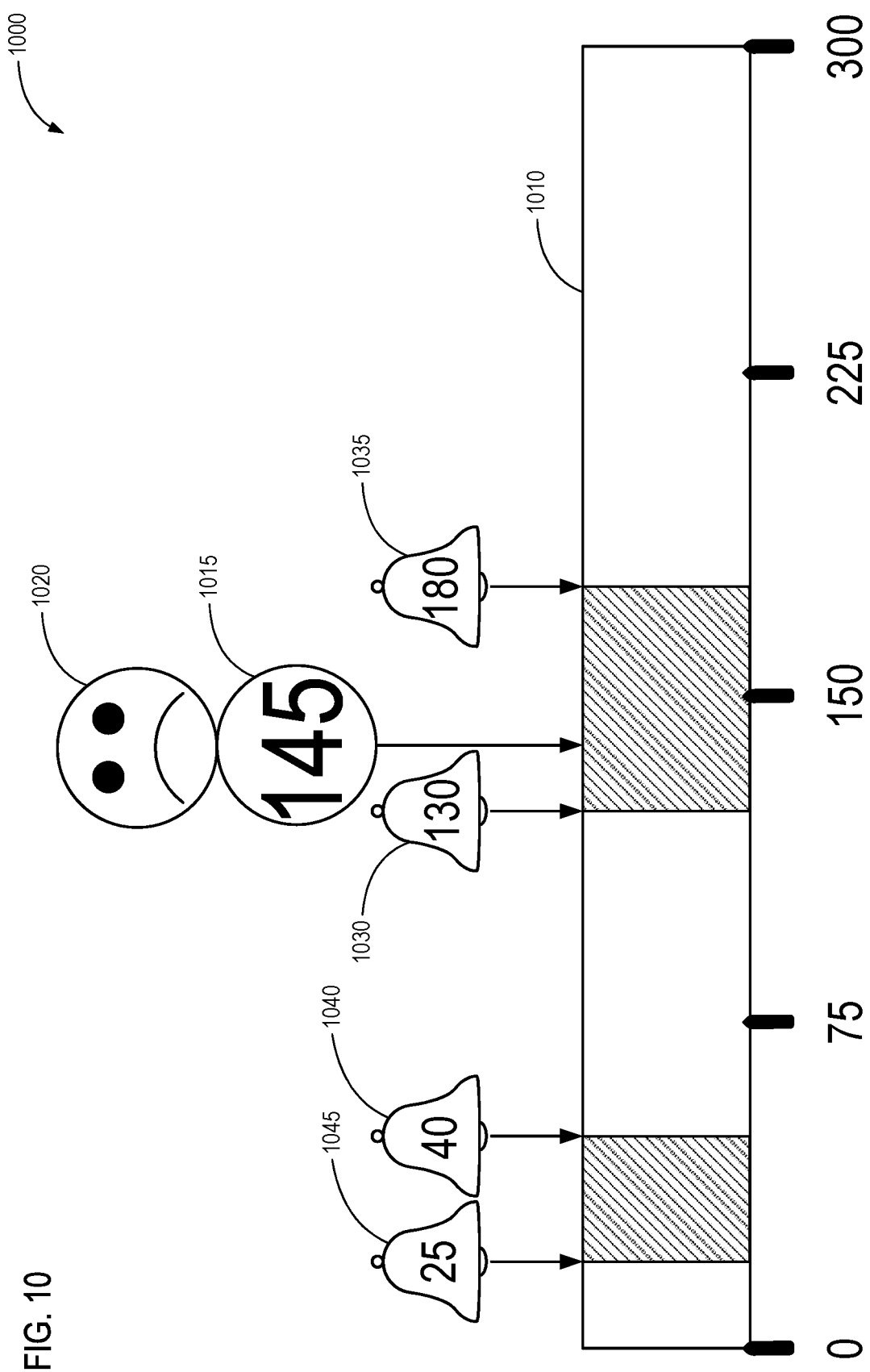
FIG. 10 illustrates a graphical display of a physiological parameter similar to FIG. 8 in a rectangular format.

FIG. 10 illustrates a graphical display 1000 of a current value 1015 along a rectangular gauge 1010 showing the status of a physiological parameter relative to various alarm bells or threshold values 1030, 1035, 1040, and 1045. In the illustrated example, the status icon 1020 is shown as a frowny face because the current value is outside of the acceptable zone.

Figure 11:
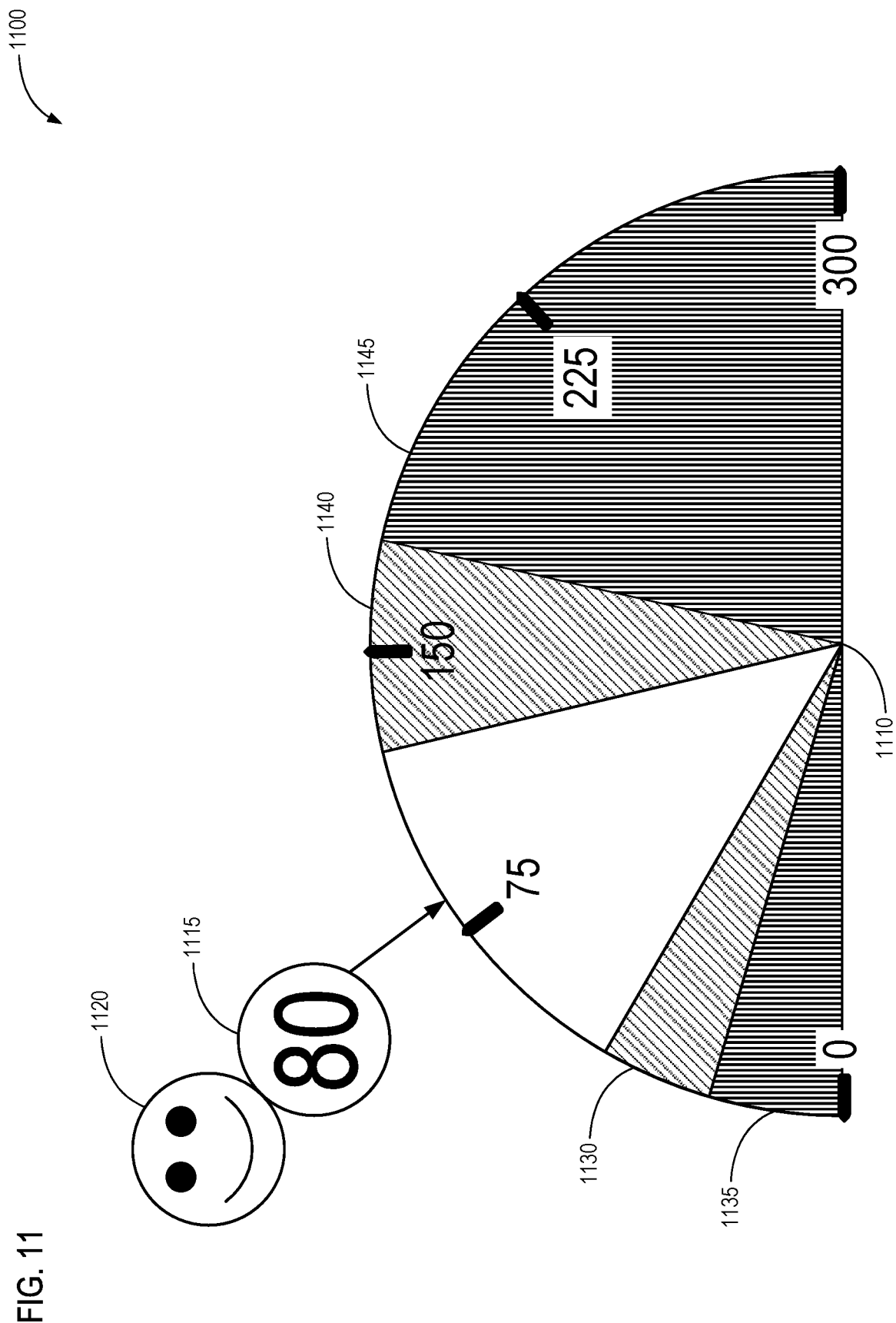
FIG. 11 illustrates a graphical display of a physiological parameter in which an icon represents an acceptable status and zones are color-coded (shaded) for acceptable, warning, and danger.

FIG. 11 illustrates a graphical display 1100 of a current value 1115 along a semicircular gauge 1110 showing the status of a physiological parameter relative to various threshold zones 1130, 1135, 1140, and 1145. In the illustrated example, the status icon 1120 is shown as a smiley face because the current value is within an acceptable zone.

Figure 12:
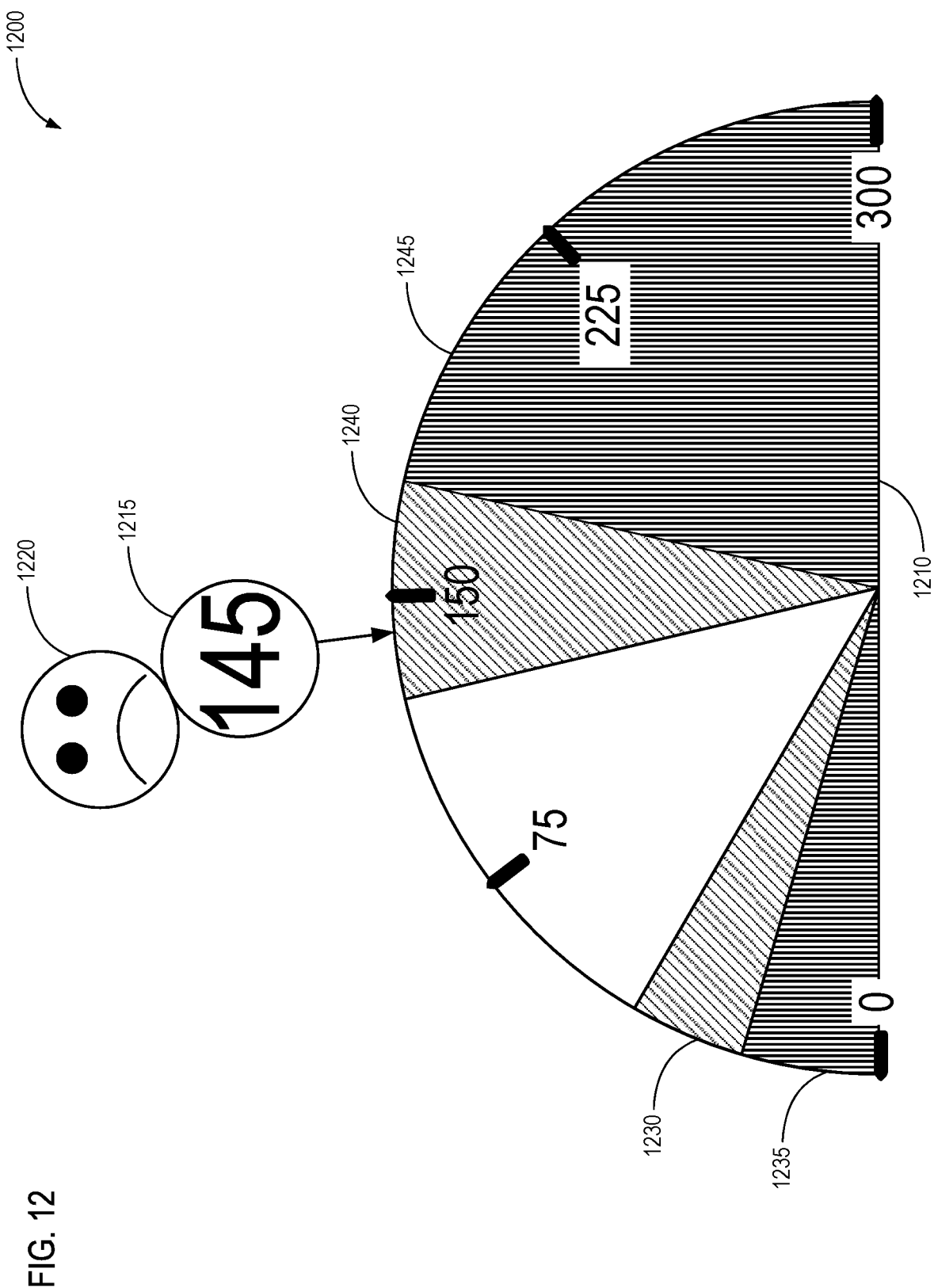
FIG. 12 illustrates a graphical display of a physiological parameter similar to that of FIG. 12 in which an icon represents that the current physiological parameter is in a warning zone.

FIG. 12 illustrates a graphical display 1200 of a current value 1215 along a semicircular gauge 1210 showing the status of a physiological parameter relative to various threshold zones 1230, 1235, 1240, and 1245. In the illustrated example, the status icon 1220 is shown as a frowny face because the current value is within a first stage of a danger zone, but not yet in a second, elevated stage of a danger zone.

Figure 13:
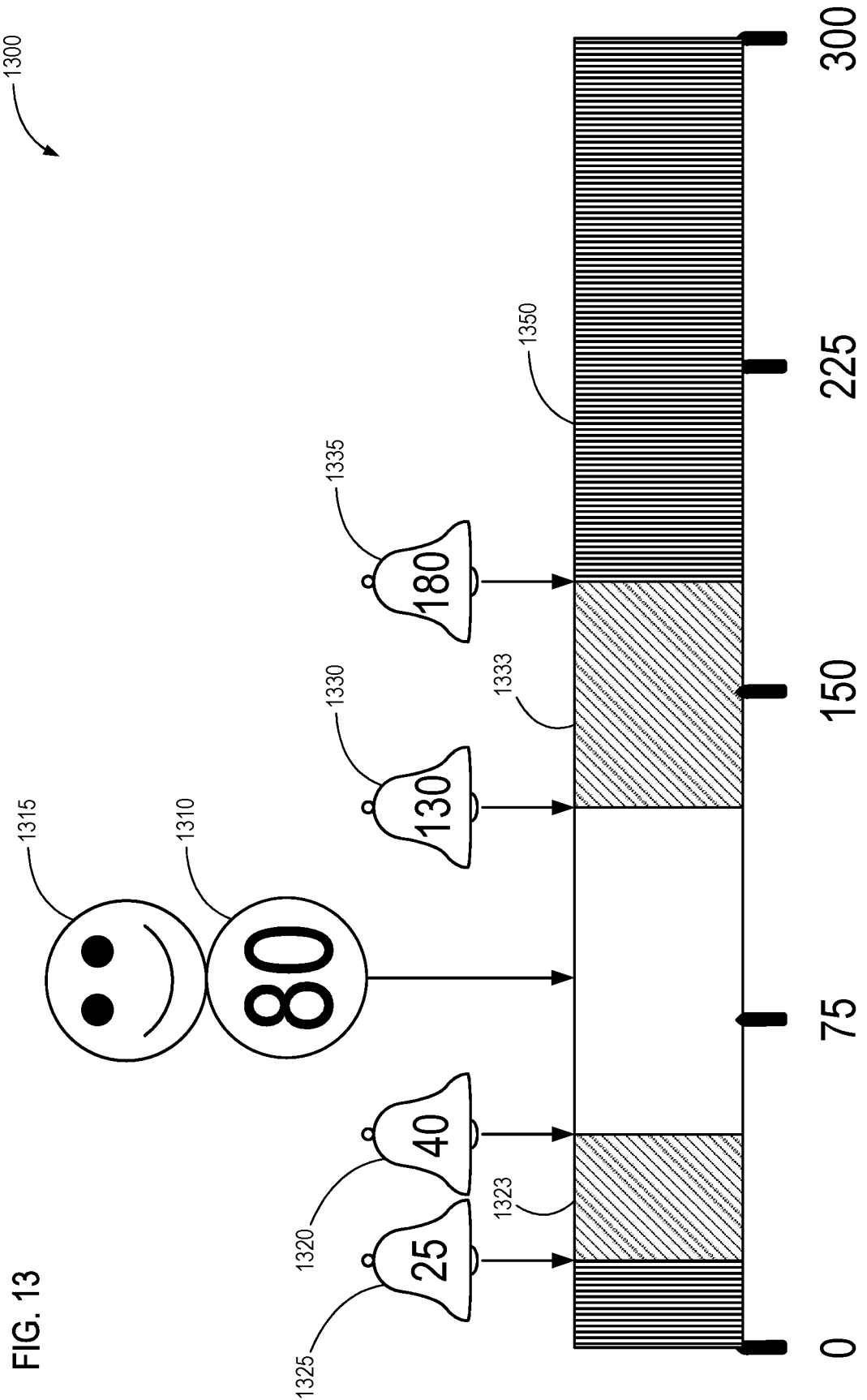
FIG. 13 illustrates a graphical display of a physiological parameter similar to that of FIG. 11 in a rectangular format.

FIG. 13 illustrates a graphical display 1300 of a current value 1310 along a rectangular gauge showing the status of a physiological parameter relative to various threshold zones 1323, 1333, and 1350. In the illustrated example, the status icon 1315 is shown as a smiley face because the current value is within an acceptable or a safe zone.

Figure 14:
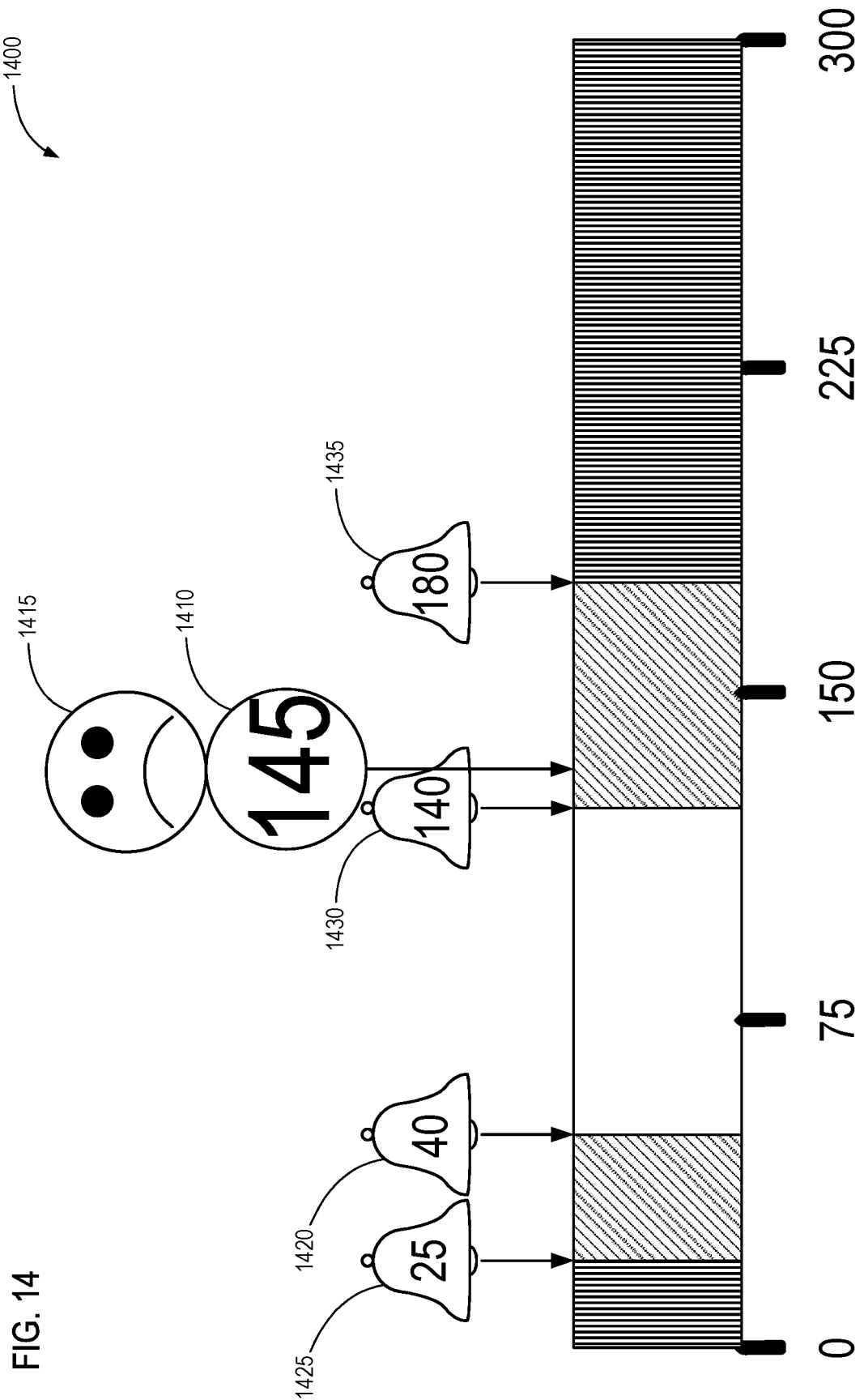
FIG. 14 illustrates a graphical display of a physiological parameter similar to that of FIG. 12 in a rectangular format.

FIG. 14 illustrates a graphical display 1400 of a current value 1410 along a rectangular gauge showing the status of a physiological parameter relative to various threshold zones. In the illustrated example, the status icon 1415 is shown as a frowny face because the current value is within a first stage of a danger zone defined by various alarm bells 1425, 1420, 1430, and 1435.

Figure 15:
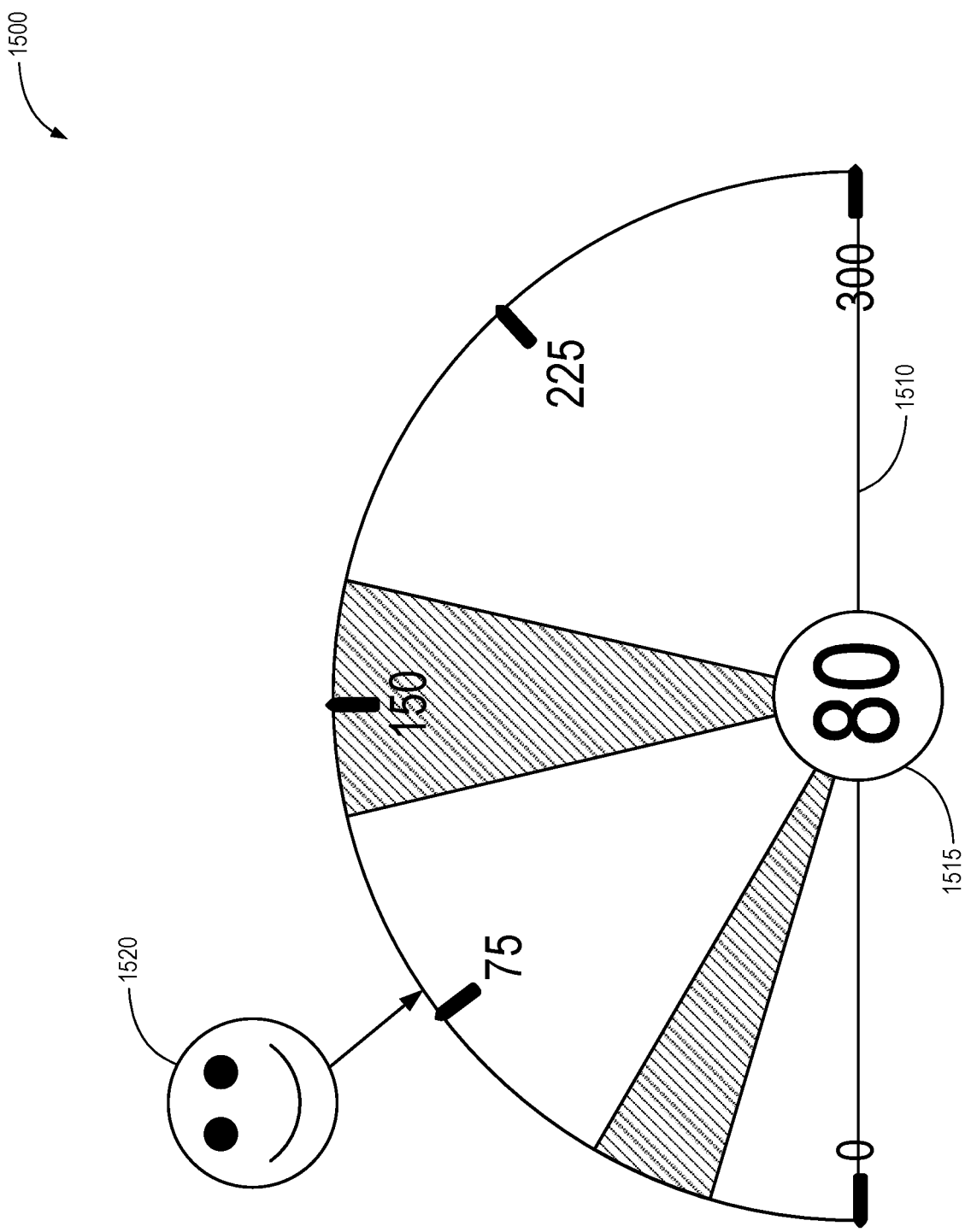
FIG. 15 illustrates a graphical display of a physiological parameter in which a current value is shown numerically in the center and graphically via a status icon around the perimeter of a semicircle.

FIG. 15 illustrates a graphical display 1500 of a physiological parameter in which a current value 1515 is shown numerically along the base of the semicircle 1510. A graphical status icon 1520 is shown along the perimeter of the semicircle 1510.

Figure 16:
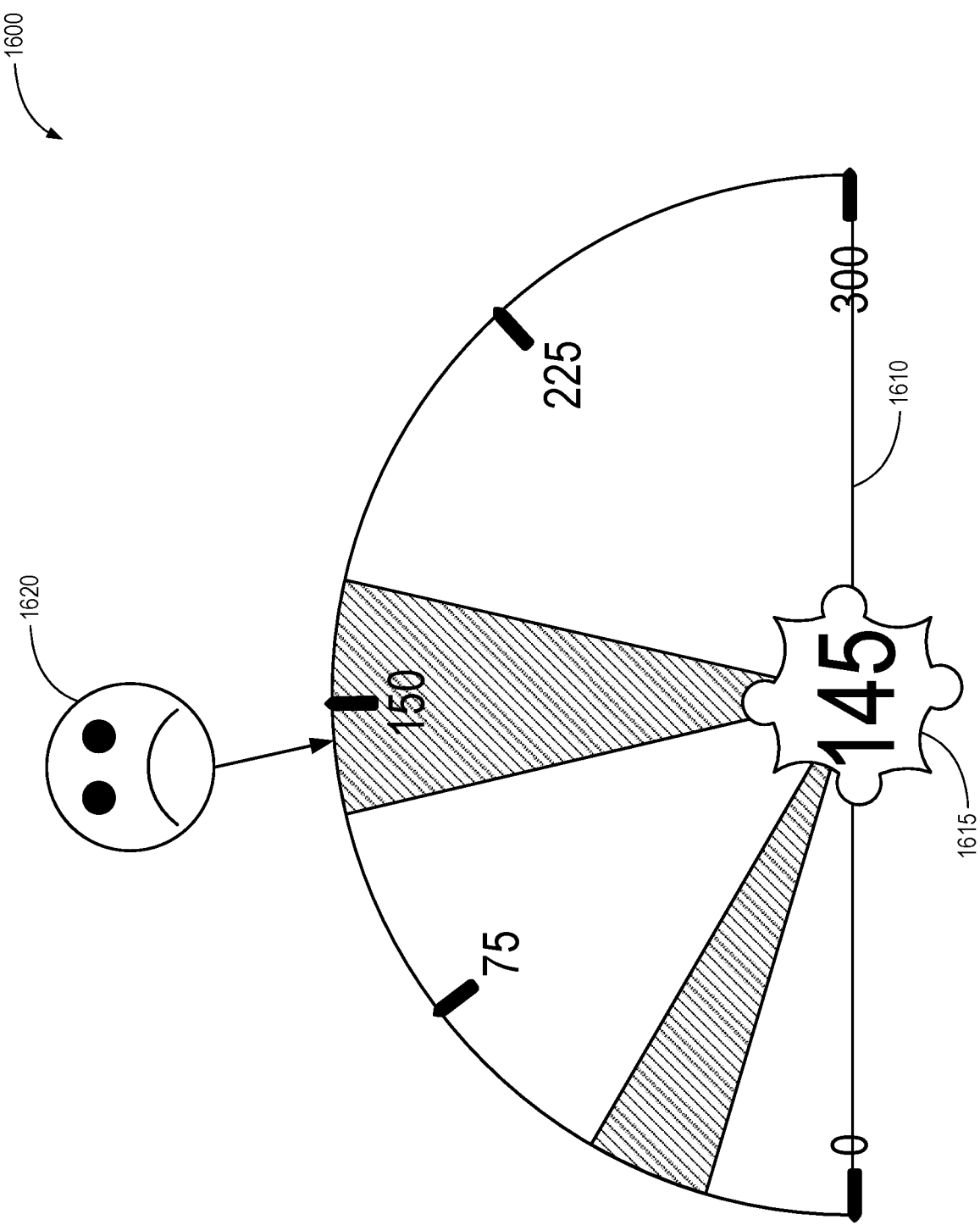
FIG. 16 is similar to FIG. 15 in which a current value of a physiological parameter is shown in the center and a status icon is shown around the perimeter of the semicircle.

FIG. 16 is similar to FIG. 15 in which a current value 1615 of a physiological parameter is shown in the center of the base of the semicircle 1610 and a status icon 1620 is shown around the perimeter of the semicircle 1610. The status icon 1620 is a frowny face to indicate that the current value 1615 is outside of an acceptable range.

Figure 17:
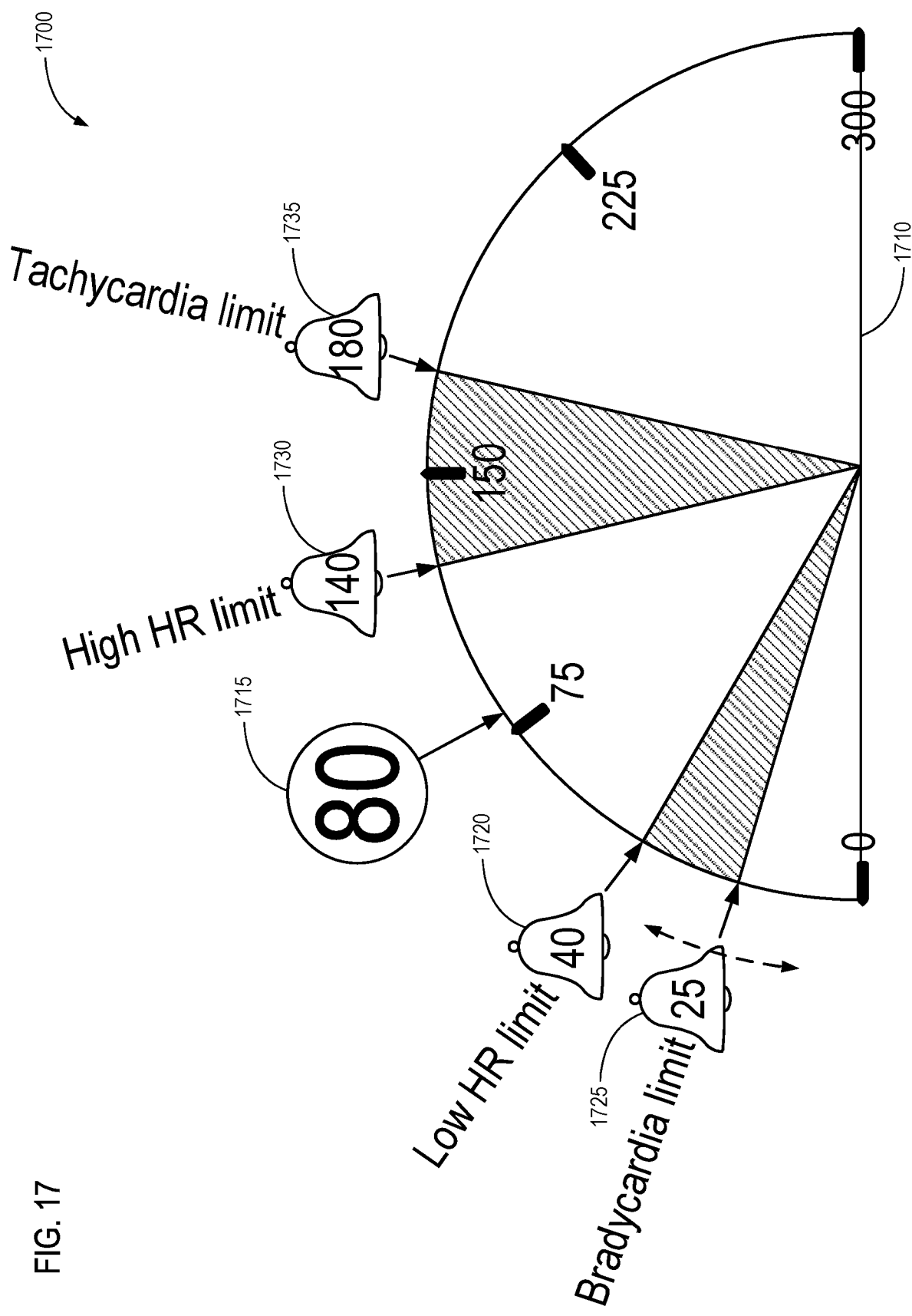
FIG. 17 illustrates a graphical display of a physiological parameter in which threshold values can be adjusted via a touchscreen interface.

FIG. 17 illustrates a graphical display 1700 of a physiological parameter in which threshold values 1720, 1725, 1730, and 1735 can be adjusted via a touchscreen interface. In various embodiments, custom alarms can be deleted, moved, renamed, changed, updated, and/or otherwise customized. A current value 1715 may be displayed as in other embodiments. The semicircle 1710 display can be modified by the user as well in various embodiments.

Figure 18:
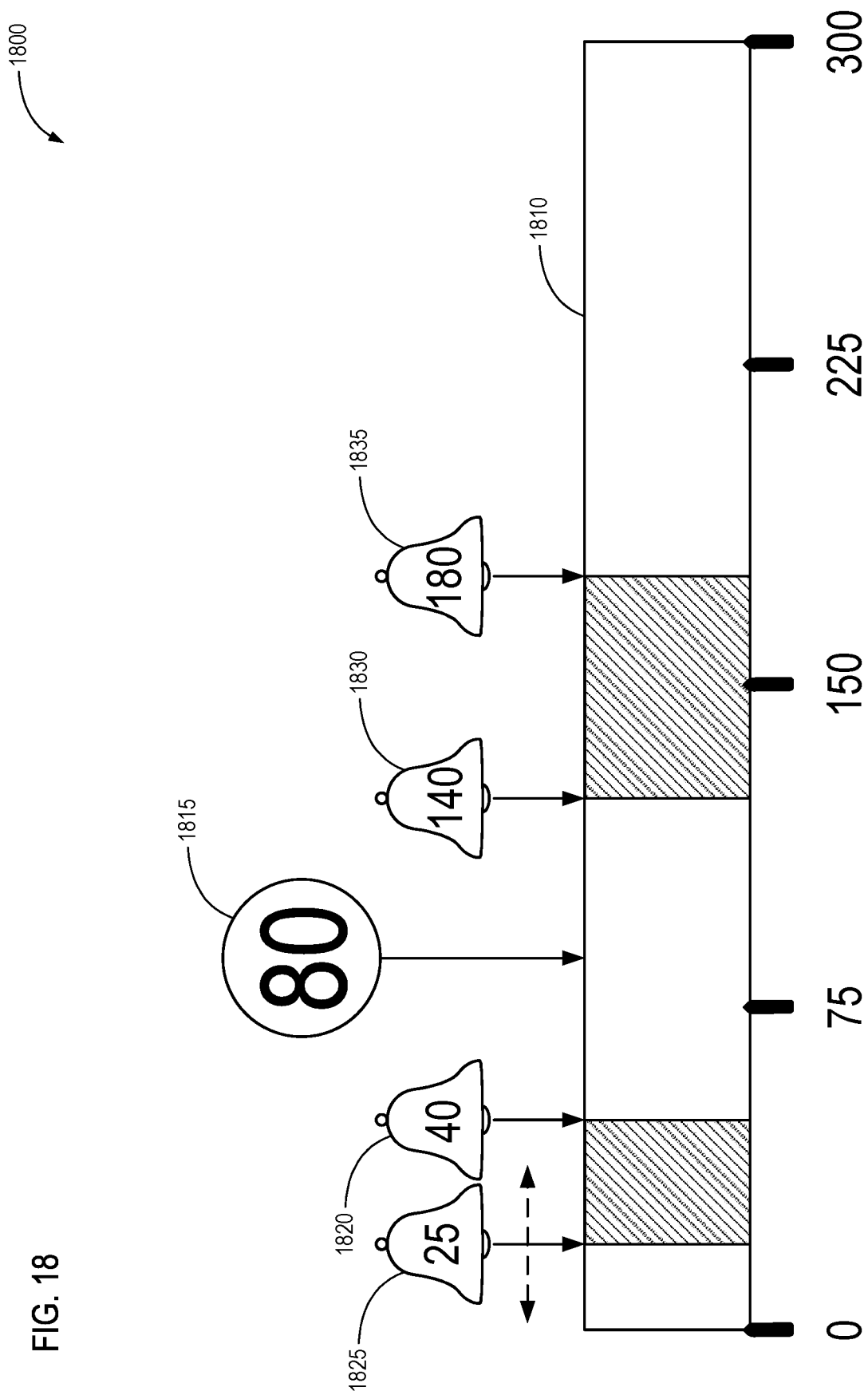
FIG. 18 illustrates a rectangular graphical display of a physiological parameter in which threshold values associated with a physiological parameter can be adjusted via a touchscreen interface.

FIG. 18 illustrates a graphical display 1800 of a physiological parameter in which threshold values 1820, 1825, 1830, and 1835 can be adjusted via a touchscreen interface. As illustrated, alarm (or threshold value) 1825 is being moved in any of the directions shown by the dashed arrows. In various embodiments, custom alarms can be deleted, moved, renamed, changed, updated, and/or otherwise customized. A current value 1815 may be displayed as in other embodiments. The rectangle 1810 display can be modified by the user as well in various embodiments. For example, it might be stretched, shortened, increased in height, and/or otherwise customized.

Figure 19:
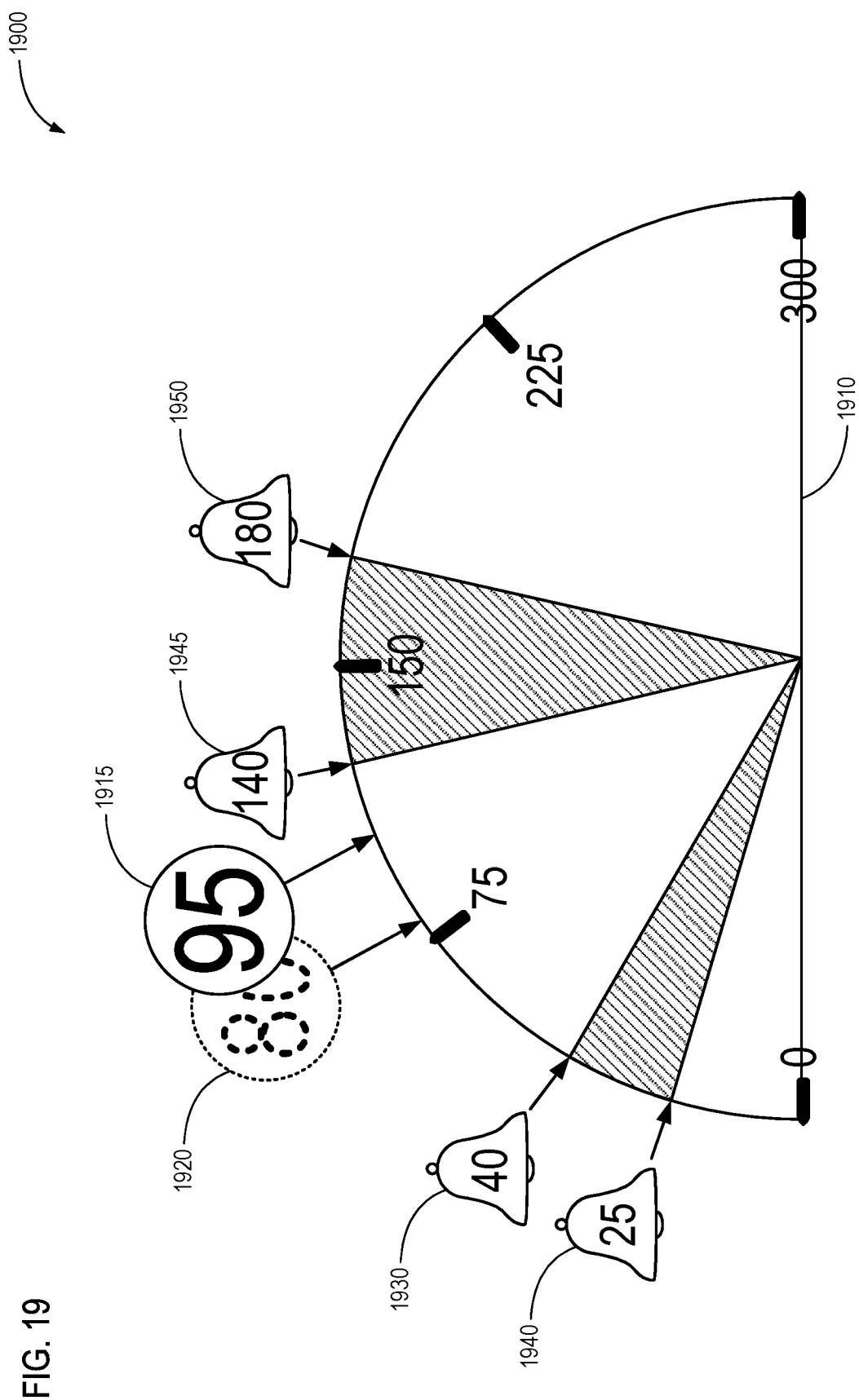
FIG. 19 illustrates a semicircle graphical display of a physiological parameter in which a ghost value is shown simultaneously with a current value.

FIG. 19 illustrates a semicircle 1910 of a graphical display 1900 of a current value 1915 of a physiological parameter in which a ghost value 1920 is shown simultaneously with the current value 1915 to provide the clinician with historical context and a view of both current and past views at the same time. The semicircle graphical display 1900 may include one or more alarms or thresholds, such as those illustrated by 1930, 1940, 1945, and 1950. The ghost value 1920 may be shown in dashed lines, as a ghost/transparent way, a different size, a different color, a different position, a different font, or other distinguishing characteristic.

Figure 20:
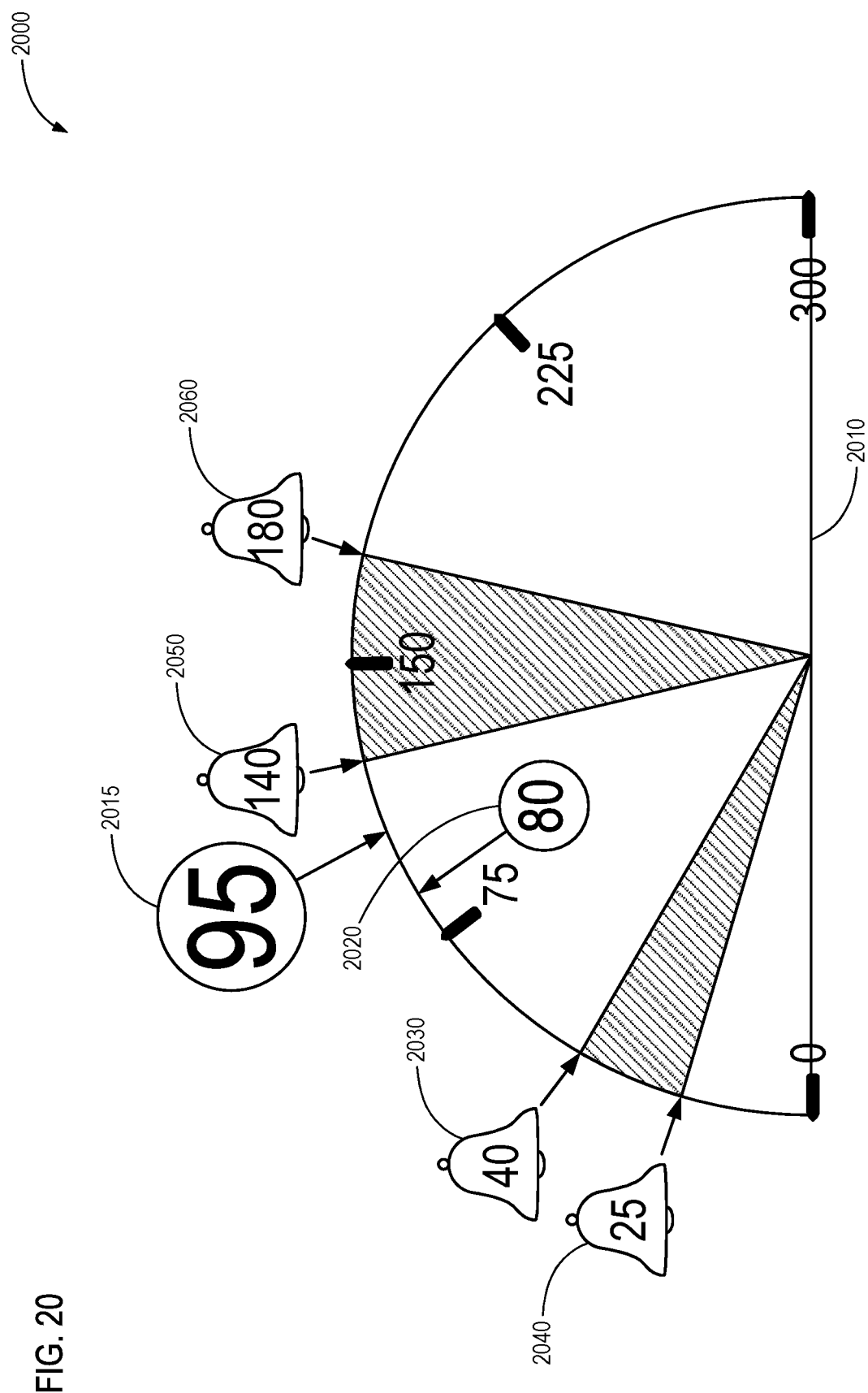
FIG. 20 illustrates an alternative semicircle graphical display of a physiological parameter in which a ghost value is shown simultaneously with the current value.

FIG. 20 illustrates an alternative semicircular gauge 2010 of a graphical display 2000 of a physiological parameter in which a historical value 2020 is shown simultaneously with the current value 2015. Various threshold values 2030, 2040, 2050, and 2060 may be shown on the graphical display and may be moved, deleted, renamed, and/or otherwise manipulated by a user (e.g., a clinician or other interested user).

Figure 21:
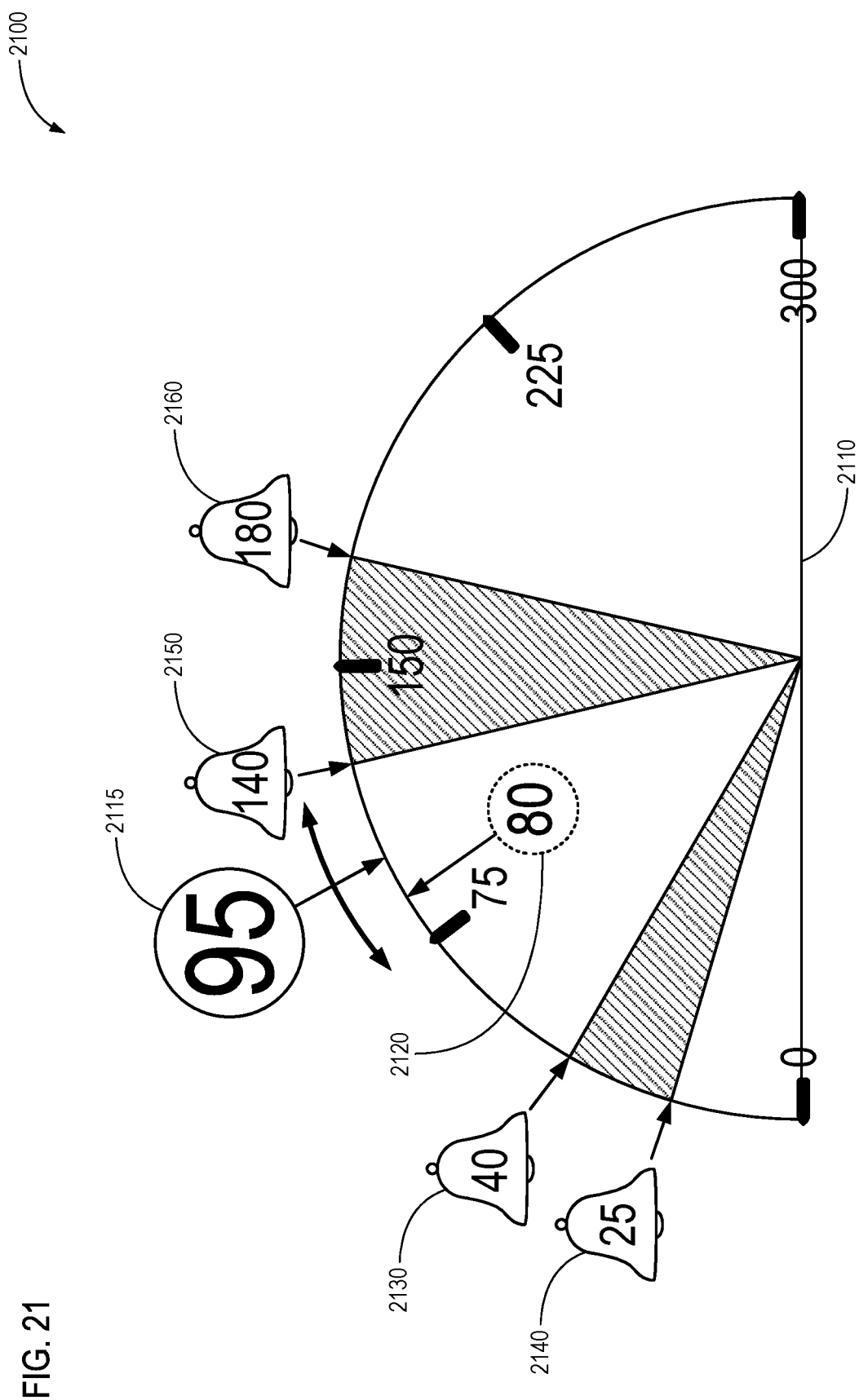
FIG. 21 illustrates a semicircle graphical display of a physiological parameter in which a range of recent variations in a current value of the physiological parameter are shown with an arrow.

FIG. 21 illustrates a semicircular gauge 2110 of a graphical display 2100 of a physiological parameter in which a range of recent variations from a current value 2115 are shown with an arrow. The arrow may extend to the right to a point corresponding to a maximum value of the physiological parameter within a recent time period. The arrow may extend to the left to a point corresponding to a minimum value of the physiological parameter within the same recent time period. The time period may be a few seconds, minutes, hours, or other period. In some embodiments, a ghost numerical value 2120 may be shown that represents an average value of the physiological parameter within the time period. As in other embodiments, alarms 2130, 2140, 2150, and 2160 represent various threshold values and may define one or more threshold, warning, or danger zones.

Figure 22:
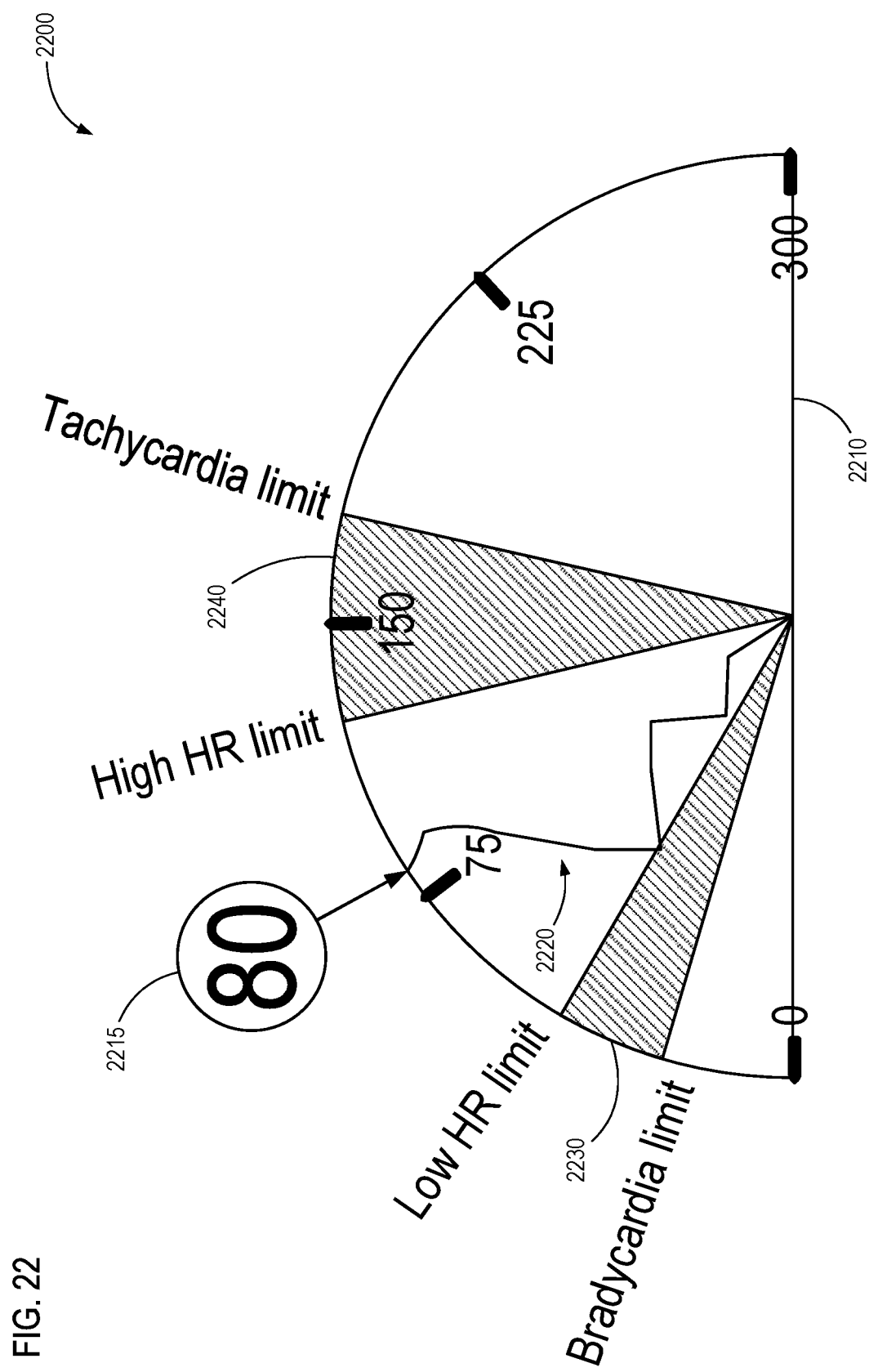
FIG. 22 illustrates a semicircle graphical display of a current physiological parameter with a line representation of historical physiological parameter values between the center and outer edges of the semicircle.

FIG. 22 illustrates a semicircular gauge 2210 of a graphical display 2200 showing various threshold zones 2230 and 2240. A current value 2215 of a physiological parameter is shown at a location along the outer perimeter of the semicircle 2210. A trend line 2220 shows historical values of the physiological parameter with the most recent values toward the perimeter of the semicircle and the oldest values of the physiological parameter toward the base of the semicircle. In some embodiments, time delineation marks may provide an indication of how long ago each historical value was sampled along the trend line 2220.

The trend line may represent a few minutes of historical values, a few seconds of historical values, or even hours, days, or weeks of historical values. In some embodiments, a user may select a point on the trend line via a touchscreen, stylus, mouse, or other device and a numerical value may be displayed. In some embodiments, numerical values for recent minimum values and recent maximum values may be displayed. In some embodiments, the trend line may be color coded based on being within one or more threshold zones 2230 and 2240. For example, a portion of trend line 2220 passing through zone 2230 may be color coded to indicate that it was below a threshold value.

The systems and methods described herein may include any combination of embodiments taught herein. For example, the trend line 2220 of FIG. 22 may be combined with the ghost values, recent range arrows, and/or other historical value indicators.

FIG. 22 illustrates a semicircular gauge 2210 of a graphical display 2200 showing various threshold zones 2230 and 2240. A current value 2215 of a physiological parameter is shown at a location along the outer perimeter of the semicircle 2210. A trend line 2220 shows historical values of the physiological parameter with the most recent values toward the perimeter of the semicircle and the oldest values of the physiological parameter toward the base of the semicircle. In some embodiments, time delineation marks may provide an indication of how long ago each historical value was sampled along the trend line 2220.

Figure 23:
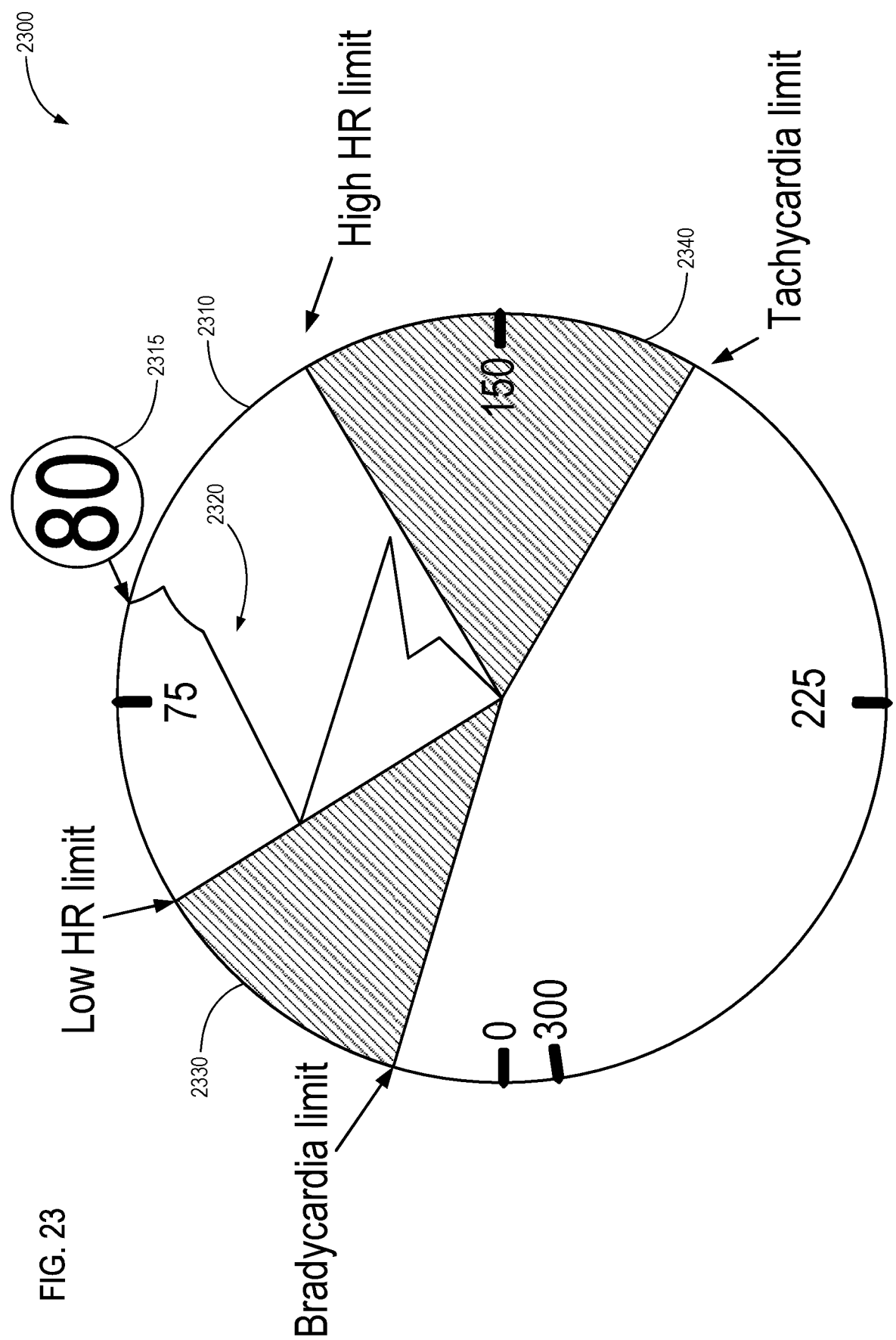
FIG. 23 illustrates a circular graphical display of a current physiological parameter similar to FIG. 22.

FIG. 23 illustrates a circular gauge 2310 of a graphical display 2300 showing a current value 2315 of a physiological parameter. The circular gauge 2310 may show an increased resolution as compared to the semicircular gauge of FIG. 22.

Figure 24:
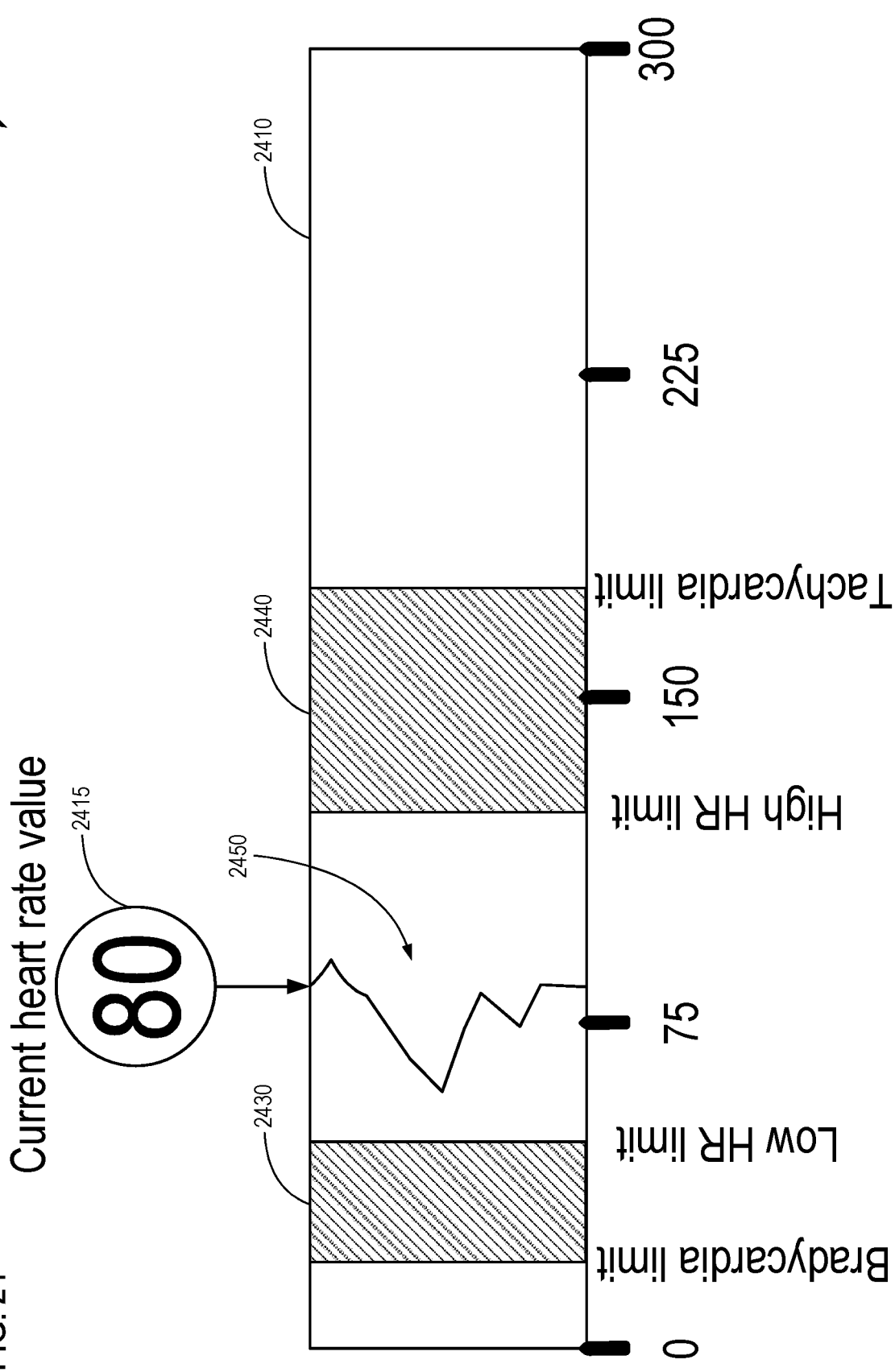
FIG. 24 illustrates a rectangular graphical display of a current physiological parameter similar to FIG. 22.

FIG. 24 illustrates a rectangular gauge 2410 of a graphical display 2400 that includes a current value 2415 of a physiological parameter along with a trend line 2450. The trend line 2450 shows historical values of the physiological parameter with the most recent values toward the top of the rectangular gauge and the older values toward the bottom of the rectangular gauge. In some embodiments, a user may adjust the time period represented by the distance between the top and bottom of the rectangular gauge and/or adjust the total height of the rectangular gauge. As in other embodiments, user-selectable alarms and threshold zones 2430 and 2440 may be shown in the graphical display 2400 as well.

Figure 25:
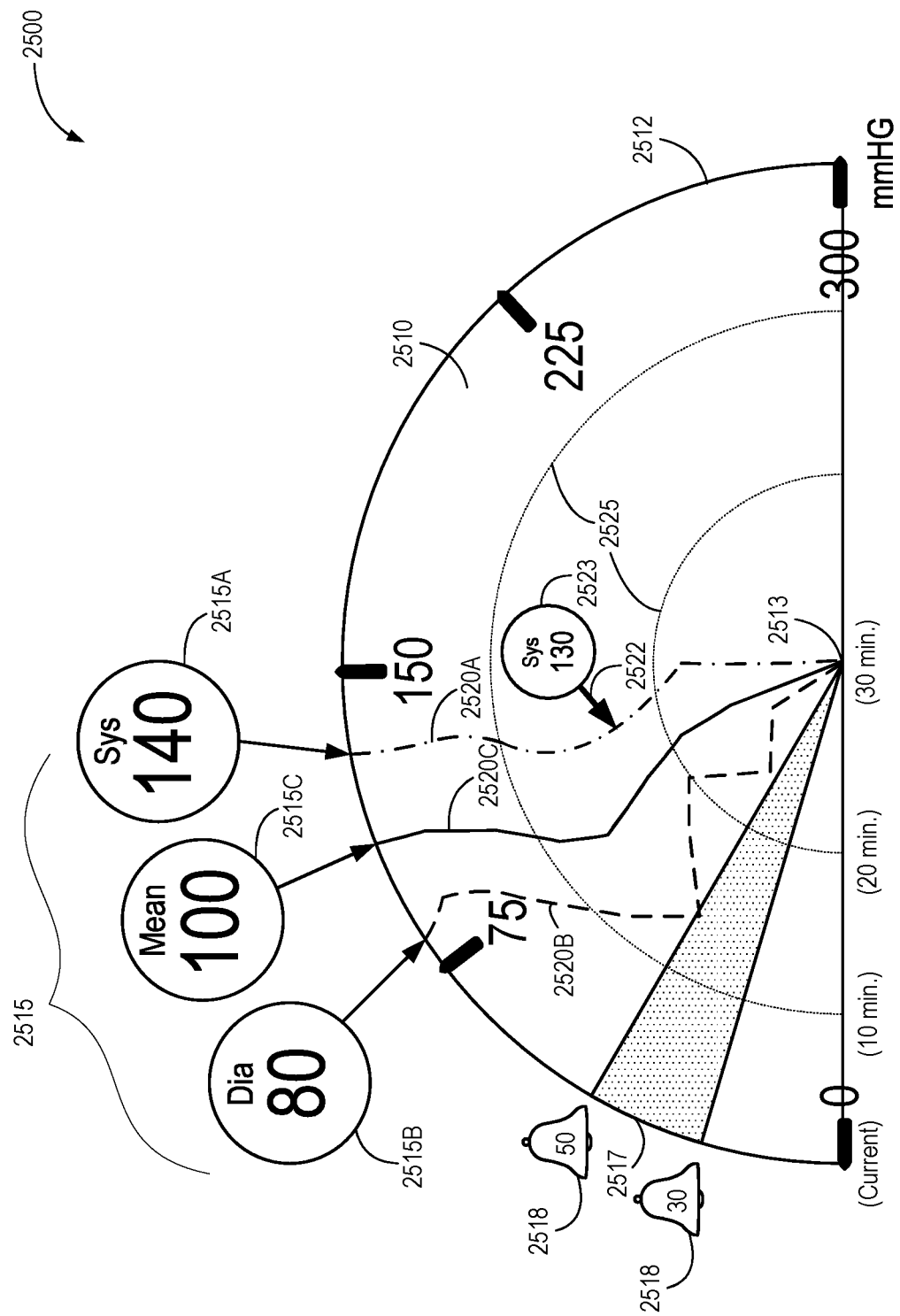
FIG. 25 illustrates a semicircular graphical display of a compound parameter with trend lines representing historical values.

FIG. 25 illustrates a semicircular gauge 2510 of a graphical display 2500 for displaying one or more physiological parameters 2515 of a patient. In one embodiment, a parameter may be a compound parameter (e.g., blood pressure), which includes multiple parameters or components, such as a systolic parameter 2515A, a diastolic parameter 2515B, and optionally, a mean 2515C of the systolic and diastolic parameters.

The outer perimeter of the semicircular gauge 2510 (referred to herein as the curved portion 2512) may represent a range of values for the physiological parameter(s) 2515 with a scale common to all parameters running between a minimum and maximum value (e.g., 0 and 300 mmHg). The scale may run in a clockwise or counterclockwise direction. A radial axis of the semicircular gauge 2510 may represent time, such that the center 2513 of the semicircular gauge 2510 corresponds to an earliest time for which historical values of a physiological parameter 2515 are represented, while the outer perimeter or curved portion 2512 corresponds to the current time.

A numerical representation of a current value of each physiological parameter 2515 may be displayed at a corresponding point along the curved portion 2512 of the semicircular gauge 2510. The numerical representations may be positioned directly on or near the semicircular gauge 2510 or within shapes, such as the circles depicted in FIG. 25. In one embodiment, arrows, lines, or other suitable indicators may be drawn from the numerical parameters 2515 (or shapes containing the parameters) to corresponding points on the scale of the curved portion 2512.

Trend lines 2520 (2520A, 2520B, 2520C) may graph historical values of the respective physiological parameters 2515A, 2515B, 2515C and originate at the center 2513 of the semicircular gauge 2510 and extend toward the curved portion 2512 thereof. In one embodiment, each trend line 2520 graphs historical values for a respective physiological parameter 2515, such that a point on the trend line 2520 representing a historical value has a radial coordinate related to time and an angular coordinate related to the historical value. The most recent values are closer to the curved portion 2512, while older values are closer to the center 2513 of the semicircular gauge 2510. In one embodiment, the center 2513 represents the time at which the oldest displayed parameter information was sampled or received, and the outer edge may represent the current time. The radius from the center 2513 to the curved portion 2512 of the semicircular gauge 2510 may represent, for example, 30 minutes of time. In some embodiments, graphical and/or numerical time delineation marks 2525 may indicate how long ago each historical value was sampled/received. Thus, the trend line 2520 may represent a few minutes of historical values, a few seconds of historical values, or even hours, days, or weeks of historical values.

In some embodiments, a user may select a point on a trend line 2520 via a touchscreen or stylus, or by moving a pointer 2522 using a mouse or other device, after which a historical value 2523 at the selected point on the trend line 2520 may be numerically displayed. A portion of the trend line 2520 may be color coded when it passes through one or more threshold zones 2517. For example, a portion of trend line 25206 may be colored red when it enters zone 2517 with a range of between 30 and 50 mmHg. As previously described, the threshold zones 2517 may be established by positioning alarm bells 2518 or other indicators or dynamically updated based on historical data. As used herein, a threshold zone 2517 may also represent a single threshold value, in which case a determination is made whether a parameter is less than, equal to, or greater than the threshold value. Thus, a zone 2517 is intended to be broadly interpreted as including one or more threshold values to specify a range or a single limit.

Those of skill in the art will recognize that the disclosed semicircular gauge 2510 emphasizes newer data, because the amplitude of a trend line 2520 becomes compressed as gets closer to the center 2513 of the semicircular gauge 2510 and thereby represents older and possibly less accurate data. However, by changing the color of the trend line 2520 if it goes into (or out of) a particular threshold zone 2517, a physician can take note of potentially dangerous historical parameter levels.

The systems and methods described herein may include any combination of embodiments taught herein. For example, the trend lines 2520 of FIG. 25 may be combined with the ghost values, recent range arrows, and/or other historical value indicators described above. Furthermore, the gauge may be represented in a shape other than a semicircle, such as a rectangle or a full circle.

Figure 26:
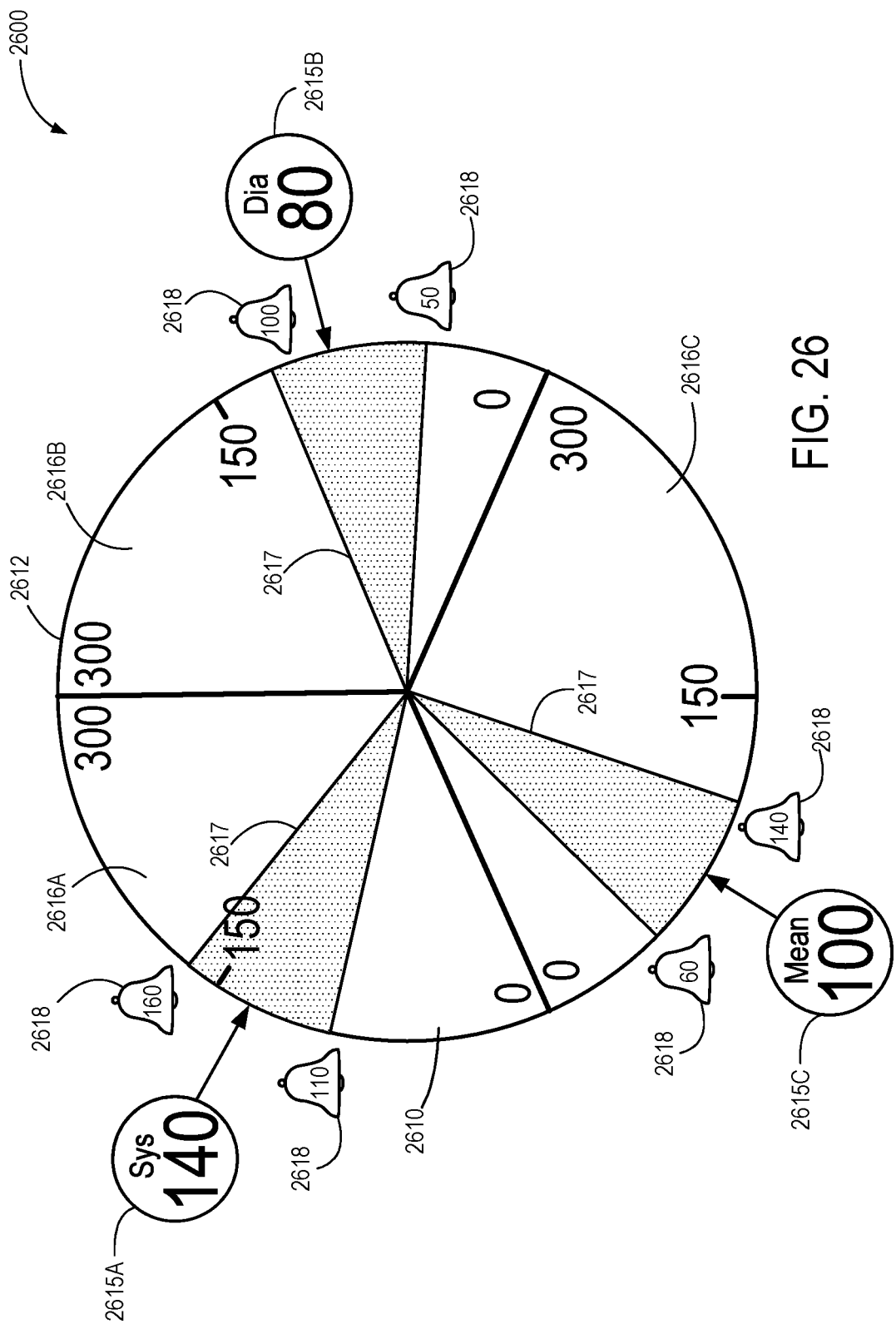
FIG. 26 illustrates a circular graphical display divided into sectors.

FIG. 26 illustrates a circular gauge 2610 of a graphical display 2600 for displaying two or more physiological parameters 2615 of a patient. In one embodiment, a parameter may be a compound parameter (e.g., blood pressure), which includes multiple parameters or components, such as a systolic parameter 2615A, a diastolic parameter 26156, and optionally, a mean 2615C of the systolic and diastolic parameters.

The circular gauge 2610 may be divided into sectors 2616 (three shown, 2616A, 2616B, 2616C), with one sector 2616 being provided for each respective parameter 2615A, 2616B, 2616C. The sectors 2616 may be of equal size in one embodiment. Thus, for an embodiment including two parameters 2615, the sectors 2616 are semicircles.

In the illustrated embodiment of FIG. 26, the circular gauge 2610 may be divided into three equal sectors 2616A-C corresponding to the systolic, diastolic, and mean parameters 2615A-C, respectively. Each sector 2616 may have an independent scale running clockwise or counterclockwise around the curved portion 2612 of the sector 2616. For example, the scale of sector 2616A may run clockwise between 0 and 300 mmHg, whereas the scales of sectors 2616B, 2616C may run counterclockwise between 0 and 300 mmHg. Of course, all scales may be oriented in the same direction in one embodiment.

A numerical representation of each parameter 2615 may be shown at a point along the curved portion 2612 of the respective sector 2616, in a manner similar to the semicircular gauge 2510 of FIG. 25. As described above, various threshold zones 2617 may be established for safe or unsafe parameters values. The threshold zones 2617 may be established, in one embodiment, by allowing a user to move or place alarm bells 2618 at corresponding points along the curved portion 2612 of a sector 2616. Of course, threshold zones 2617 may be established in other ways, such as by historical patient data. In one embodiment, if the value of a parameter 2615 leaves and/or enters a threshold zone 2617, a visual and/or audible alert may be presented to warn medical personnel. Various color coding may also be applied to attract attention, as previously described. As used herein, a threshold zone 2617 may also represent a single threshold value, in which case a determination is made whether a parameter is less than, equal to, or greater than the threshold value. Thus, a zone 2617 is intended to be broadly interpreted as including one or more threshold values to specify a range or a single limit.

By dividing the circular gauge 2610 into sectors 2616, multiple parameters 2615 may be represented within the circular gauge 2610 along with threshold zones 2617, alarm bells 2618, and the like without becoming confusing to medical personnel. As a person of skill in the art can appreciate, displaying multiple unrelated parameters 2615 within the same scale could create overlapping values that make the gauge 2610 difficult to read. Even when multiple components of a compound parameter 2515 (e.g., blood pressure) are represented within the same scale, displaying threshold zones 2617 may be complicated by the fact that some of the zones may overlap. The use of separate sectors 2616 with independent scales solves this problem.

Figure 27:
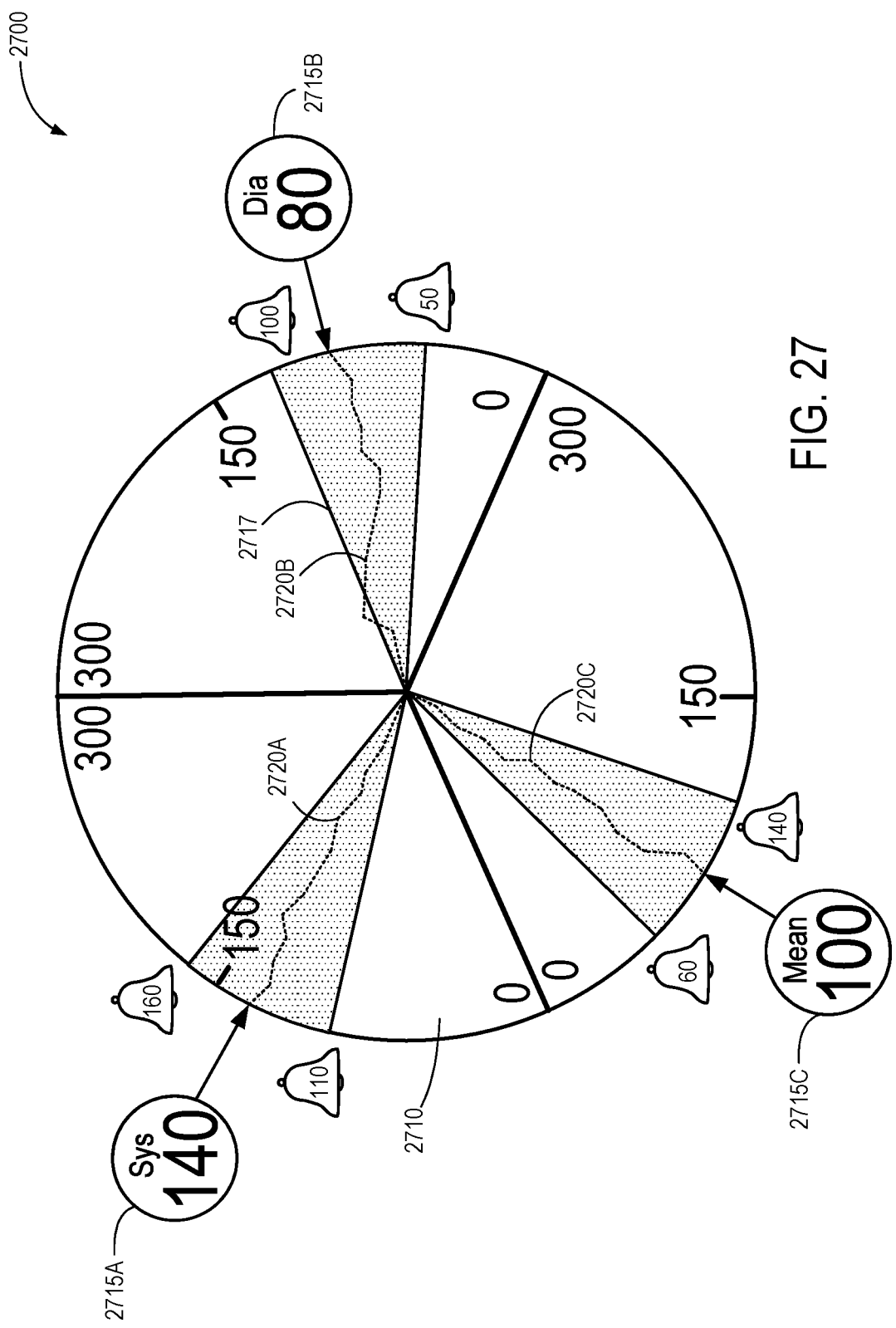
FIG. 27 illustrates a circular graphical display divided into sectors including trend lines representing historical values.

FIG. 27 illustrates a circular gauge 2710 of a graphical display 2700 for displaying two or more physiological parameters of a patient. In one embodiment, a parameter may be a compound parameter 2715 (e.g., blood pressure), which includes multiple parameters or components, such as a systolic parameter 2715A, a diastolic parameter 27156, and optionally, a mean 2715C of the systolic and diastolic parameters.

FIG. 27 is similar in all respects to FIG. 26 except for the inclusion of trend lines 2720 (three shown, 2720A, 2720B, 2720C). The trend lines 2720 function similarly to those described in connection with the semicircular gauge 2510 of FIG. 25. The trend lines 2720A-C may show historical values of the respective physiological parameter 2720A-C, which extend radially from the center, with the most recent values being represented toward the perimeter of the circular gauge 2710 and the oldest values being represented toward the center of the semicircular gauge 2710. Thus, the trend lines 2720 emphasize newer data, because the amplitude of a trend line 2720 becomes compressed as gets closer to the center of the circular gauge 2710 and thereby represents older and possibly less accurate data. However, as discussed with reference to FIG. 25, by changing the color of a portion of the trend line 2720 if it goes into (or out of) a particular threshold zone 2717, a physician can take note of potentially dangerous historical parameter levels.

Figure 28:
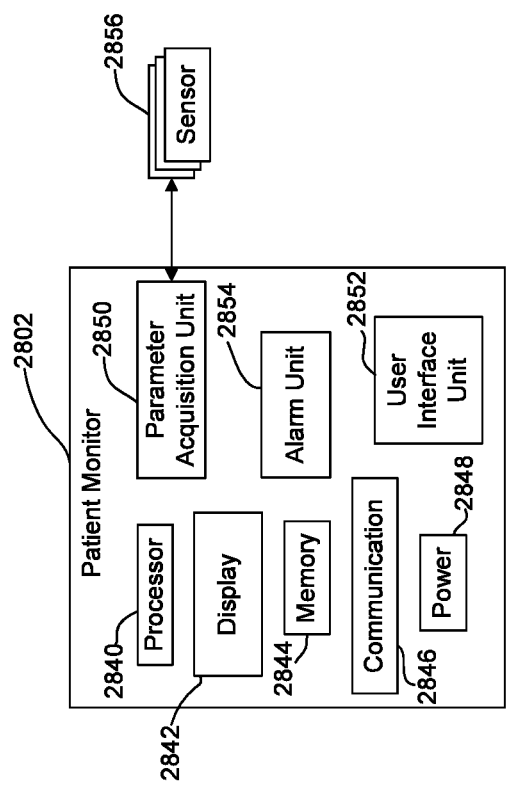
FIG. 28 is a block diagram of a patient monitoring system.

FIG. 28 is a block diagram of a patient monitor 2802, which analyzes and display physiological parameters, such as pulse rate, temperature, respiration rate, blood pressure, blood oxygen, electrocardiogram, and the like. The patient monitor 2802, according to the example embodiment illustrated in FIG. 28, includes a processor 2840, a display device 2842, a memory device 2844, a communication device 2846, a power module 2848, a parameter acquisition unit 2850, a user interface unit 2852, and an alarm unit 2854.

The processor 2840 is configured to process patient data signals received from one or more sensors 2856 through the parameter acquisition unit 2850 and to display the patient data signals (e.g., as waveforms and/or numerical values) on the display device 2842. The parameter acquisition unit 2850 may be configured to process the acquired patient data signals in cooperation with the processor 2840. The patient monitor 2822 may store the patient data signals in the memory device 2844 along with other data. For example, the patient monitor 2822 may store a current set of configuration settings in the memory device 2844. The memory device 2844 may be implemented using various types of volatile or non-volatile memory, such as a random access memory (RAM), a hard disk drive, or the like. The power unit 2848 provides any necessary power conversions and distributes power throughout the patient monitor 2822.

The user interface unit 2852, in cooperation with the processor 2840 and the display device 2842, may be configured to process and format the acquired physiological parameters for display in a graphical user interface (GUI) as shown in FIGS. 1-27. The alarm unit 2854 may be configured to generate audible and/or visual alarms when physiological parameters for a local patient are outside of a determined range. The alarm information may include, for example, location information for the remote patient and an alarm condition indicated by the one or more physiological parameters that are outside of a determined range. The alarm unit 2854, in cooperation with the processor 2840, display device 2842, and user interface unit 2852, may display the alarm information within the GUI.

An artisan will recognize from the disclosure herein that the parameter acquisition unit 2850, user interface unit 2852, and/or alarm unit 2854 may be combined with the processor 2840 into a single unit. Further, the processor 2840, parameter acquisition unit 2850, user interface unit 2852, and/or alarm unit 2854, either combined or separately, may include a special purpose processor configured to perform the processes described herein. In another embodiment, the processor 2840, parameter acquisition unit 2850, user interface unit 2852, and/or alarm unit 2854, either combined or separately, may include a general purpose processor configured to execute computer-executable instructions (e.g., stored in a computer-readable medium, such as the memory device 2844) to perform the processes described herein.

Reference has been made to various exemplary embodiments, including the best mode. However, those skilled in the art will recognize that changes and modifications may be made to the exemplary embodiments without departing from the scope of the present disclosure. While the principles of this disclosure have been shown in various embodiments, many modifications of structure, arrangements, proportions, elements, materials, and components may be adapted for a specific environment and/or operating requirements without departing from the principles and scope of this disclosure. These and other changes or modifications are intended to be included within the scope of the present disclosure.

This disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element. The scope of the present invention should, therefore, be determined by the following claims.

What is claimed is:

1. A system for displaying physiological parameters, the system comprising:
    a parameter acquisition unit that receives one or more physiological parameters of a patient from one or more sensors;
    a memory device that stores historical values of the one or more physiological parameters received by the parameter acquisition unit;
    a user interface unit that displays representations of current and historical values of the one or more physiological parameters in a graphical user interface (GUI), wherein the GUI comprises:
        a semicircular gauge having a curved portion representing a common range of values for the one or more physiological parameters and a radial axis representing time, a center of the semicircular gauge corresponding to an earliest time for which a historical value is represented within the semicircular gauge and the curved portion corresponding to a current time, wherein the curved portion includes a common numerical scale for the one or more physiological parameters;
        a numerical representation of a current value of each physiological parameter displayed at a corresponding point along the curved portion of the semicircular gauge;
        a trend line for each physiological parameter originating at the center of the semicircular gauge and extending toward the curved portion thereof, wherein each trend line graphs historical values for a respective physiological parameter, wherein a point on the trend line representing a historical value has a radial coordinate corresponding to a time at which the historical value is sampled and an angular coordinate corresponding to the historical value, wherein each historical value is readable on the semicircular gauge as a function of the angular coordinate and the radial coordinate of a graphed point on the trend line with respect to the common numerical scale.

2. The system of claim 1, wherein the one or more physiological parameters comprise a compound parameter including multiple components.

3. The system of claim 2, wherein the compound parameter is blood pressure and the multiple components include a systolic component and a diastolic component.

4. The system of claim 1, wherein each numerical representation is displayed outside of the curved portion, and a line or arrow is drawn from the numerical representation to a corresponding point along the curved portion of the semicircular gauge.

5. The system of claim 1, wherein each numerical representation is displayed within a geometric shape disposed next to the curved portion.

6. The system of claim 5, wherein the geometric shape comprises a circle.

7. The system of claim 1, wherein the GUI further includes one or more time delineation marks within the semicircular gauge indicating an amount of time before the current time at which a historical value represented on a trend line was received.

8. The system of claim 1, wherein, in response to a user selecting a point on a trend line for a physiological parameter, the user interface unit displays a corresponding historical value of physiological parameter at the selected point.

9. The system of claim 1, wherein the GUI further comprises one or more threshold zones including one or more threshold values specifying a range or a single limit.

10. The system of claim 9, wherein the user interface unit color codes at least a portion of a trend line that passes into the one or more threshold zones.

11. The system of claim 1, wherein the one or more threshold zones are established in response to a user setting or positioning alarm bells along the curved portion.

12. The system of claim 1, wherein the GUI further comprises an icon shown as a smiling face, a straight face or a frowning face that indicates whether or not the current value of the physiological parameter is in an acceptable range.

13. The system of claim 1, wherein the GUI further comprises a numerical representation of a ghost value shown simultaneously with the current value to provide the user with historical context and a view of both current and past views at the same time.

14. The system of claim 13, wherein the ghost value is shown by dashed lines, transparency, a different size, a different color, a different position, or a different font.

15. The system of claim 1, wherein the GUI further comprises an arrow which shows a range of recent variations from the current value.

16. The system of claim 1, wherein the GUI further comprises numerical values for recent minimum and maximum values.

17. The system of claim 1, wherein the numerical representation is positioned on or near the semicircular gauge and is optionally encircled.

18. The system of claim 1, wherein the GUI further comprises indicators drawn from the one or more physiological parameters to corresponding points on the curved portion of the semicircular gauge or on the trend line.

19. The system of claim 18, wherein the indicators includes arrows and lines.

20. A method for displaying physiological parameters, the method comprising:
receiving or more physiological parameters of a patient from one or more sensors;
storing historical values of the one or more physiological parameters received from the one or more sensors in a memory device;
displaying representations of current and historical values of the one or more physiological parameters in a graphical user interface (GUI), wherein the GUI comprises:
a semicircular gauge having a curved portion representing a common range of values for the one or more physiological parameters and a radial axis representing time, a center of the semicircular gauge corresponding to an earliest time for which a historical value is represented within the semicircular gauge and the curved portion corresponding to a current time, wherein the curved portion includes a common numerical scale for the one or more physiological parameters;
a numerical representation of a current value of each physiological parameter displayed at a corresponding point along the curved portion of the semicircular gauge;
a trend line for each physiological parameter originating at the center of the semicircular gauge and extending toward the curved portion thereof, wherein each trend line graphs historical values for a respective physiological parameter, wherein a point on the trend line representing a historical value has a radial coordinate corresponding to a time at which the historical value is sampled and an angular coordinate corresponding to the historical value, wherein each historical value is readable on the semicircular gauge as a function of the angular coordinate and the radial coordinate of a graphed point on the trend line with respect to the common numerical scale.

21. The method of claim 20, wherein the one or more physiological parameters comprise a compound parameter including multiple components.

22. The method of claim 21, wherein the compound parameter is blood pressure and the multiple components include a systolic component and a diastolic component.

23. The method of claim 20, wherein each numerical representation is displayed outside of the curved portion, and a line or arrow is drawn from the numerical representation to a corresponding point along the curved portion of the semicircular gauge.

24. The method of claim 20, wherein each numerical representation is displayed within a geometric shape disposed next to the curved portion.

25. The method of claim 24, wherein the geometric shape comprises a circle.

26. The method of claim 20, wherein the GUI further includes one or more time delineation marks within the semicircular gauge indicating an amount of time before the current time at which a historical value represented on a trend line was received.

27. The method of claim 20, wherein, in response to a user selecting a point on a trend line for a physiological parameter, the user interface unit displays a corresponding historical value of physiological parameter at the selected point.

28. The method of claim 20, wherein the GUI further comprises one or more threshold zones including one or more threshold values specifying a range or a single limit.

29. The method of claim 19, wherein the user interface unit color codes at least a portion of a trend line that passes into the one or more threshold zones.

30. The method of claim 20, wherein the one or more threshold zones are established in response to a user setting or positioning alarm bells along the curved portion.

31. The method of claim 20, wherein the GUI further comprises an icon shown as a smiling face, a straight face or a frowning face that indicates whether or not the current value of the physiological parameter is in an acceptable range.

32. The method of claim 20, wherein the GUI further comprises a numerical representation of a ghost value shown simultaneously with the current value to provide the user with historical context and a view of both current and past views at the same time.

33. The method of claim 32, wherein the ghost value is shown by dashed lines, in a ghost or transparent way, a different size, a different color, a different position or a different font.

34. The method of claim 20, wherein the GUI further comprises an arrow which shows a range of recent variations from the current value.

35. The method of claim 20, wherein the GUI further comprises numerical values for recent minimum and maximum values.

36. The method of claim 20, wherein the numerical representation is positioned on or near the semicircular gauge and is optionally encircled.

37. The method of claim 20, wherein the GUI further comprises indicators drawn from the one or more physiological parameters to corresponding points on the curved portion of the semicircular gauge or on the trend line.

38. The method of claim 37, wherein the indicators includes arrows and lines.

* * * * *